(12) United States Patent
Choi et al.

(10) Patent No.: US 9,249,210 B2
(45) Date of Patent: Feb. 2, 2016

(54) RECOMBINANT EXPRESSION VECTOR SYSTEM FOR VARIANTS OF COAGULATION FACTOR VIII AND VON WILLEBRAND FACTOR

(71) Applicant: Korea University Industrial & Academic Collaborative Foundation, Seoul (KR)

(72) Inventors: Sang Yun Choi, Seoul (KR); Sang Won Park, Sungnam (KR)

(73) Assignee: Korea University Industrial & Academic Collaborative Foundation, Seoul (KR)

( * ) Notice: Subject to any disclaimer, the term of this patent is extended or adjusted under 35 U.S.C. 154(b) by 0 days.

(21) Appl. No.: 14/291,713

(22) Filed: May 30, 2014

(65) Prior Publication Data

US 2015/0005473 A1 Jan. 1, 2015

Related U.S. Application Data

(62) Division of application No. 12/200,928, filed on Aug. 28, 2008, now Pat. No. 8,791,247.

(30) Foreign Application Priority Data

Feb. 29, 2008 (KR) .................... 10-2008-0019392

(51) Int. Cl.
*C07H 21/04* (2006.01)
*C07K 14/755* (2006.01)

(52) U.S. Cl.
CPC .................... *C07K 14/755* (2013.01)

(58) Field of Classification Search
None
See application file for complete search history.

(56) References Cited

U.S. PATENT DOCUMENTS

| 5,250,421 | A | 10/1993 | Kaufman et al. | |
|---|---|---|---|---|
| 5,994,136 | A | 11/1999 | Naldini et al. | |
| 8,791,247 | B2 * | 7/2014 | Choi et al. | 536/23.5 |

FOREIGN PATENT DOCUMENTS

| KR | 10-0251286 B1 | 4/2000 |
|---|---|---|
| WO | WO-86/06096 A1 | 10/1986 |
| WO | WO-86/06101 A1 | 10/1986 |

OTHER PUBLICATIONS

Peake et al. Severe Type III von Willebrand's Disease Caused by Deletion of Exon 42 . . . Blood. 1990, vol. 75, No. 3, pp. 654-661.*

(Continued)

*Primary Examiner* — Jeffrey E Russel
(74) *Attorney, Agent, or Firm* — Mintz Levin Cohn Ferris Glovsky and Popeo, P.C.; Kongsik Kim; Elaine V. Morlock

(57) ABSTRACT

Disclosed is an expression vector system for variants of coagulation Factor VIII (FVIII) and von Willebrand Factor (vWF). In detail, mutant vWF the size of which is significantly reduced by deleting exons but which has remarkably increased FVIII stabilizing and activating efficiency, and an expression vector system useful for the treatment of hemophilia which is capable of expressing the same along with FVIII are disclosed. Use of the mutant vWF with a reduced size enables effective expression of FVIII in a viral vector and significantly enhanced FVIII activity. Further, the viral vector may be effectively used to treat hemophilia through gene therapy.

3 Claims, 14 Drawing Sheets

(56) References Cited

OTHER PUBLICATIONS

Burns, J.C., et al., "Vesicular stomatitis virus G glucoprotein pseudotyped retroviral vectors: Concentration to very high titer and efficient gene transfer into mammalian and nonmamalian cells", *Proc. Natl. Acad. Sci. USA*, vol. 90, pp. 8033-8037 (Sep. 1993).

De Meyer, et al, "Phenotypic correction of von Willebrand disease type 3 blood-derived endothelial cells with lentiviral vectors expressing von Willebrand factor," *Blood*, 107: 4728-4736 (2006).

Hofmann et al., "Species-Specific, Postentry Barriers to Primate Immunodeficiency Virus Infection", *Journal of Virology*, pp. 10020-10028 (Dec. 1999).

James et al, "A novel type 2A von Willebrand factor mutation located at the last nucleotide of exon 26 (3538G>A) causes skipping of 2 nonadjacent exons", *Blood*, 104: 2739-2745 (2004).

Lavergne et al., "Primary structure of the Factor VIII binding domain of human, porcine and rabbit von Willebrand factor." *Biochem. Biophys. Res. Commun.* 194:1019-1024, 1993.

Mancuso et al., "Structure of the gene for human von Willebrand factor." *J. Biol. Chem.* 264:19514-19527, 1989.

Park et al., "A Stable Gene Transfer System for Hematopoietic Progenitor Cells from Human Bone Marrow Using Pseudotyped Retroviral Vectors", *Mol. Cells*, vol. 17, No. 2, pp. 297-303. (2004).

Park et al., "Long term expression of von Willebrand Factor by a VSV-G pseudotyped lentivirus enhances the funstional activity of secreted B-domain-deleted coagulation factor VIII." *Molecules and Cells* 24:125-131, Aug. 31, 2007.

Petrus et al., "Gene therapy strategies for hemophilia: benefits versus risks." *J. Gene Med.* 12: 797-809, 2010.

Sadler "Biochemistry and Genetics of Von Willebrand Factor", *Annu. Rev. Biochem.*, 67: 395-424 (1998).

Walsh et al., "Hemophilia clinical gene therapy: brief review". *Translation Research*. 161:307-312, 2013.

\* cited by examiner

SEQUENCE LISTING

```
<160> NUMBER OF SEQ ID NOS: 19

<210> SEQ ID NO 1
<211> LENGTH: 3564
<212> TYPE: DNA
<213> ORGANISM: Homo sapiens

<400> SEQUENCE: 1
atgattcctg ccagatttgc cggggtgctg cttgctctgg ccctcatttt gccagggacc        60
ctttgtgcag aaggaactcg cggcaggtca tccacggccc gatgcagcct tttcggaagt       120
gacttcgtca acacctttga tgggagcatg tacagctttg cgggatactg cagttacctc       180
ctggcagggg gctgccagaa acgctccttc tcgattattg gggacttcca gaatggcaag       240
agagtgagcc tctccgtgta tcttggggaa ttttttgaca tccatttgtt tgtcaatggt       300
accgtgacac aggggggacca aagagtctcc atgccctatg cctccaaagg gctgtatcta       360
gaaactgagg ctgggtacta caagctgtcc ggtgaggcct atggctttgt ggccaggatc       420
gatggcagcg gcaactttca agtcctgctg tcagacagat acttcaacaa gacctgcggg       480
ctgtgtggca actttaacat ctttgctgaa gatgacttta tgacccaaga agggaccttg       540
acctcggacc cttatgactt tgccaactca tgggctctga gcagtggaga acagtggtgt       600
gaacgggcat ctcctcccag cagctcatgc aacatctcct ctgggaaat gcagaagggc       660 ctgtgggagc agtgccagct tctgaagagc acctcggtgt tgcccgctg ccaccctctg       720 gtggaccccg agccttttgt ggccctgtgt gagaagactt tgtgtgagtg tgctgggggg       780
ctggagtgcg cctgccctgc cctcctggag tacgcccgga cctgtgccca ggagggaatg       840
gtgctgtacg gctggaccga ccacagcgcg tgcagcccaa tgtgccctgc tggtatggag       900
tataggcagt gtgtgtcccc ttgcgccagg acctgccaga gcctgcacat caatgaaatg       960
tgtcaggagc gatgcgtgga tggctgcagc tgccctgagg acagctcct ggatgaaggc      1020 ctctgcgtgg agagcaccga gtgtccctgc gtgcattccg gaaagcgcta ccctccggc       1080 acctccctct ctcgagactg caacacctgc atttgccgaa acagccagtg gatctgcagc      1140
aatgaagaat gtccagggga gtgccttgtc acaggtcaat cacacttcaa gagctttgac      1200
aacagatact tcaccttcag tgggatctgc cagtacctgc tggcccggga ttgccaggac      1260
cactccttct ccattgtcat tgagactgtc cagtgtgctg atgaccgcga cgctgtgtgc      1320
acccgctccg tcaccgtccg gctgcctggc ctgcacaaca gccttgtgaa actgaagcat      1380
ggggcaggag ttgccatgga tggccaggac gtccagctcc cctcctgaa aggtgacctc      1440 cgcatccagc atacagtgac ggcctccgtg cgcctcagct acgggagga cctgcagatg      1500 gactgggatg gccgcgggag gctgctggtg aagctgtccc ccgtctatgc cgggaagacc      1560
tgcggcctgt gtgggaatta caatggcaac cagggcgacg acttccttac cccctctggg      1620
ctggcggagc ccgggtgga ggacttcggg aacgcctgga agctgcacgg ggactgccag      1680
gacctgcaga agcagcacag cgatccctgc gccctcaacc cgcgcatgac caggttctcc      1740
```

```
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggcctgcg cggggagagg cgtgcgcgtc    1920
gcgtggcgcg agccaggccg ctgtgagctg aactgcccga aggccaggt gtacctgcag     1980 tgcgggaccc cctgcaacct gacctgccgc tctctctctt acccggatga ggaatgcaat    2040
gaggcctgcc tggagggctg cttctgcccc ccagggctct acatggatga ggggggggac   2100
tgcgtgccca aggccagtg cccctgttac tatgacggtg agatcttcca gccagaagac    2160
atcttctcag accatcacac catgtgctac tgtgaggatg gcttcatgca ctgtaccatg    2220
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc ccccgggca tggtccggca tgagaacaga    2460
tgtgtggccc tggaaaggtg tccctgcttc atcagggca aggagtatgc ccctggagaa    2520
acagtgaaga ttggctgcaa cacttgtgtc tgtcaggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga ccttttcggat cctagtggga ataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg gaattttgat    3000
ggcatccaga acaatgacct caccagcagc aacctccaag tggaggaaga ccctgtggac    3060
tttgggaact cctggaaagt gagctcgcag tgtgctgaca ccagaaaacg tgatgagacg    3120
ctccaggatg gctgtgatac tcacttctgc aaggtcaatg agagaggaga gtacttctgg    3180
gagaagaggg tcacaggctg cccacccttt gatgaacaca gtgtctggc tgagggaggt    3240 aaaattatga aaattccagg cacctgctgt gacacatgtg aggagcctga gtgcaacgac    3300
atcactgcca ggctgcagta tgtcaaggtg ggaagctgta agtctgaagt agaggtggat    3360
atccactact gccagggcaa atgtgccagc aaagccatgt actccattga catcaacgat    3420
gtgcaggacc agtgctcctg ctgctctccg acacggacgg agcccatgca ggtggccctg    3480
cactgcacca atggctctgt tgtgtaccat gaggttctca atgccatgga gtgcaaatgc    3540
tcccccagga agtgcagcaa gtga                                           3564
```

<210> SEQ ID NO 2
<211> LENGTH: 1187
<212> TYPE: PRT
<213> ORGANISM: Homo sapiens

<400> SEQUENCE: 2

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45
```

```
Ser Met Tyr Ser Phe Ala Gly Tyr Cys Ser Tyr Leu Leu Ala Gly Gly
    50              55                  60
Cys Gln Lys Arg Ser Phe Ser Ile Ile Gly Asp Phe Gln Asn Gly Lys
 65              70                  75                  80
Arg Val Ser Leu Ser Val Tyr Leu Gly Glu Phe Phe Asp Ile His Leu
                85                  90                  95
Phe Val Asn Gly Thr Val Thr Gln Gly Asp Gln Arg Val Ser Met Pro
            100                 105                 110
Tyr Ala Ser Lys Gly Leu Tyr Leu Glu Thr Glu Ala Gly Tyr Tyr Lys
        115                 120                 125
Leu Ser Gly Glu Ala Tyr Gly Phe Val Ala Arg Ile Asp Gly Ser Gly
130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Met Thr Gln
                165                 170                 175
Glu Gly Thr Leu Thr Ser Asp Pro Tyr Asp Phe Ala Asn Ser Trp Ala
            180                 185                 190
Leu Ser Ser Gly Glu Gln Trp Cys Glu Arg Ala Ser Pro Pro Ser Ser
        195                 200                 205
Ser Cys Asn Ile Ser Ser Gly Glu Met Gln Lys Gly Leu Trp Glu Gln
210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
                245                 250                 255
Cys Ala Gly Gly Leu Glu Cys Ala Cys Pro Ala Leu Leu Glu Tyr Ala
            260                 265                 270
Arg Thr Cys Ala Gln Glu Gly Met Val Leu Tyr Gly Trp Thr Asp His
        275                 280                 285
Ser Ala Cys Ser Pro Val Cys Pro Ala Gly Met Glu Tyr Arg Gln Cys
290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
            340                 345                 350
Ser Gly Lys Arg Tyr Pro Pro Gly Thr Ser Leu Ser Arg Asp Cys Asn
        355                 360                 365
Thr Cys Ile Cys Arg Asn Ser Gln Trp Ile Cys Ser Asn Glu Glu Cys
370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
            420                 425                 430
Ala Asp Asp Arg Asp Ala Val Cys Thr Arg Ser Val Thr Val Arg Leu
        435                 440                 445
Pro Gly Leu His Asn Ser Leu Val Lys Leu Lys His Gly Ala Gly Val
450                 455                 460
```

```
Ala Met Asp Gly Gln Asp Val Gln Leu Pro Leu Leu Lys Gly Asp Leu
465                 470                 475                 480
Arg Ile Gln His Thr Val Thr Ala Ser Val Arg Leu Ser Tyr Gly Glu
                485                 490                 495
Asp Leu Gln Met Asp Trp Asp Gly Arg Gly Arg Leu Leu Val Lys Leu
                500                 505                 510
Ser Pro Val Tyr Ala Gly Lys Thr Cys Gly Leu Cys Gly Asn Tyr Asn
                515                 520                 525
Gly Asn Gln Gly Asp Asp Phe Leu Thr Pro Ser Gly Leu Ala Glu Pro
                530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
                565                 570                 575
Thr Arg Phe Ser Glu Glu Ala Cys Ala Val Leu Thr Ser Pro Thr Phe
                580                 585                 590
Glu Ala Cys His Arg Ala Val Ser Pro Leu Pro Tyr Leu Arg Asn Cys
                595                 600                 605
Arg Tyr Asp Val Cys Ser Cys Ser Asp Gly Arg Glu Cys Leu Cys Gly
                610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
                645                 650                 655
Val Tyr Leu Gln Cys Gly Thr Pro Cys Asn Leu Thr Cys Arg Ser Leu
                660                 665                 670
Ser Tyr Pro Asp Glu Glu Cys Asn Glu Ala Cys Leu Glu Gly Cys Phe
                675                 680                 685
Cys Pro Pro Gly Leu Tyr Met Asp Glu Arg Gly Asp Cys Val Pro Lys
                690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Met Ser Gly Val Pro Gly Ser Leu Leu Pro Asp Ala Val
                740                 745                 750
Leu Ser Ser Pro Leu Ser His Arg Ser Lys Arg Ser Leu Ser Cys Arg
                755                 760                 765
Pro Pro Met Val Lys Leu Val Cys Pro Ala Asp Asn Leu Arg Ala Glu
                770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
                805                 810                 815
His Glu Asn Arg Cys Val Ala Leu Glu Arg Cys Pro Cys Phe His Gln
                820                 825                 830
Gly Lys Glu Tyr Ala Pro Gly Glu Thr Val Lys Ile Gly Cys Asn Thr
                835                 840                 845
Cys Val Cys Gln Asp Arg Lys Trp Asn Cys Thr Asp His Val Cys Asp
                850                 855                 860
Ala Thr Cys Ser Thr Ile Gly Met Ala His Tyr Leu Thr Phe Asp Gly
865                 870                 875                 880
```

Leu Lys Tyr Leu Phe Pro Gly Glu Cys Gln Tyr Val Leu Val Gln Asp
            885                 890                 895

Tyr Cys Gly Ser Asn Pro Gly Thr Phe Arg Ile Leu Val Gly Asn Lys
        900                 905                 910

Gly Cys Ser His Pro Ser Val Lys Cys Lys Arg Val Thr Ile Leu
        915                 920                 925

Val Glu Gly Gly Glu Ile Glu Leu Phe Asp Gly Glu Val Asn Val Lys
        930                 935                 940

Arg Pro Met Lys Asp Glu Thr His Phe Glu Val Glu Ser Gly Arg
945                 950                 955                 960

Tyr Ile Ile Leu Leu Gly Lys Ala Leu Ser Val Val Trp Asp Arg
        965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
            995                 1000                1005

Ser Ser Asn Leu Gln Val Glu Glu Asp Pro Val Asp Phe Gly Asn
        1010                1015                1020

Ser Trp Lys Val Ser Ser Gln Cys Ala Asp Thr Arg Lys Arg Asp
        1025                1030                1035

Glu Thr Leu Gln Asp Gly Cys Asp Thr His Phe Cys Lys Val Asn
        1040                1045                1050

Glu Arg Gly Glu Tyr Phe Trp Glu Lys Arg Val Thr Gly Cys Pro
        1055                1060                1065

Pro Phe Asp Glu His Lys Cys Leu Ala Glu Gly Gly Lys Ile Met
        1070                1075                1080

Lys Ile Pro Gly Thr Cys Cys Asp Thr Cys Glu Glu Pro Glu Cys
        1085                1090                1095

Asn Asp Ile Thr Ala Arg Leu Gln Tyr Val Lys Val Gly Ser Cys
        1100                1105                1110

Lys Ser Glu Val Glu Val Asp Ile His Tyr Cys Gln Gly Lys Cys
        1115                1120                1125

Ala Ser Lys Ala Met Tyr Ser Ile Asp Ile Asn Asp Val Gln Asp
        1130                1135                1140

Gln Cys Ser Cys Cys Ser Pro Thr Arg Thr Glu Pro Met Gln Val
        1145                1150                1155

Ala Leu His Cys Thr Asn Gly Ser Val Val Tyr His Glu Val Leu
        1160                1165                1170

Asn Ala Met Glu Cys Lys Cys Ser Pro Arg Lys Cys Ser Lys
        1175                1180                1185

<210> SEQ ID NO 3
<211> LENGTH: 5508
<212> TYPE: DNA
<213> ORGANISM: Homo sapiens

<400> SEQUENCE: 3
atgattcctg ccagatttgc cggggtgctg cttgctctgg ccctcatttt gccagggacc     60
ctttgtgcag aaggaactcg cggcaggtca tccacggccc gatgcagcct tttcggaagt    120
gacttcgtca acacctttga tgggagcatg tacagctttg cgggatactg cagttacctc    180
ctggcagggg gctgccagaa acgctccttc tcgattattg ggacttccag aatggcaag    240 agagtgagcc tctccgtgta tcttggggaa ttttttgaca tccatttgtt tgtcaatggt    300
accgtgacac agggggacca aagagtctcc atgcccctatg cctccaaagg gctgtatcta    360

```
gaaactgagg ctgggtacta caagctgtcc ggtgaggcct atggctttgt ggccaggatc    420
gatggcagcg gcaactttca agtcctgctg tcagacagat acttcaacaa gacctgcggg    480
ctgtgtggca actttaacat cttttgctgaa gatgacttta tgacccaaga agggaccttg    540
acctcggacc cttatgactt tgccaactca tgggctctga gcagtggaga acagtggtgt    600
gaacgggcat ctcctcccag cagctcatgc aacatctcct ctggggaaat gcagaagggc    660
ctgtgggagc agtgccagct tctgaagagc acctcggtgt ttgcccgctg ccaccctctg    720
gtggaccccg agccttttgt ggccctgtgt gagaagactt tgtgtgagtg tgctgggggg    780
ctggagtgcg cctgccctgc cctcctggag tacgcccgga cctgtgccca ggagggaatg    840
gtgctgtacg gctggaccga ccacagcgcg tgcagcccag tgtgccctgc tggtatggag    900
tataggcagt gtgtgtcccc ttgcgccagg acctgccaga gcctgcacat caatgaaatg    960
tgtcaggagc gatgcgtgga tggctgcagc tgccctgagg acagctcct  ggatgaaggc   1020 ctctgcgtgg agagcaccga gtgtccctgc gtgcattccg aaagcgcta cccctcccggc  1080 acctccctct ctcgagactg caacacctgc atttgccgaa acagccagtg gatctgcagc   1140
aatgaagaat gtccagggga gtgccttgtc acaggtcaat cacacttcaa gagctttgac   1200
aacagatact tcaccttcag tgggatctgc cagtacctgc tggcccggga ttgccaggac   1260
cactccttct ccattgtcat tgagactgtc cagtgtgctg atgaccgcga cgctgtgtgc   1320
acccgctccg tcaccgtccg gctgcctggc ctgcacaaca gccttgtgaa actgaagcat   1380
ggggcaggag ttgccatgga tggccaggac gtccagctcc ccctcctgaa aggtgacctc   1440
cgcatccagc atacagtgac ggcctccgtg cgcctcagct acggggagga cctgcagatg   1500
gactgggatg gccgcgggag gctgctggtg aagctgtccc ccgtctatgc cgggaagacc   1560
tgcggcctgt gtgggaatta caatggcaac cagggcgacg acttccttac cccctctggg   1620
ctggcggagc cccgggtgga ggacttcggg aacgcctgga agctgcacgg ggactgccag   1680
gacctgcaga agcagcacag cgatcccgtc gccctcaacc cgcgcatgac caggttctcc   1740
gaggaggcgt gcgcggtcct gacgtccccc acattcgagg cctgccatcg tgccgtcagc   1800
ccgctgccct acctgcggaa ctgccgctac gacgtgtgct cctgctcgga cggccgcgag   1860
tgcctgtgcg gcgccctggc cagctatgcc gcggcctgcg cggggagagg cgtgcgcgtc   1920
gcgtggcgcg agcaggccg ctgtgagctg aactgcccga aaggccaggt gtacctgcag   1980
tgcgggaccc cctgcaacct gacctgccgc tctctctctt acccggatga ggaatgcaat   2040
gaggcctgcc tggagggctg cttctgcccc ccagggctct acatggatga gggggggac   2100 tgcgtgccca aggcccagtg cccctgttac tatgacggtg agatcttcca gccagaagac   2160
atcttctcag accatcacac catgtgctac tgtgaggatg gcttcatgca ctgtaccatg   2220
agtggagtcc ccggaagctt gctgcctgac gctgtcctca gcagtcccct gtctcatcgc   2280
agcaaaagga gcctatcctg tcggcccccc atggtcaagc tggtgtgtcc cgctgacaac   2340
ctgcgggctg aagggctcga gtgtaccaaa acgtgccaga actatgacct ggagtgcatg   2400
agcatgggct gtgtctctgg ctgcctctgc ccccgggca tggtccggca tgagaacaga   2460
tgtgtggccc tggaaaggtg tccctgcttc catcagggca aggagtatgc ccctggagaa   2520
acagtgaaga ttggctgcaa cacttgtgtc tgtcgggacc ggaagtggaa ctgcacagac   2580
catgtgtgtg atgccacgtg ctccacgatc ggcatggccc actacctcac cttcgacggg   2640
ctcaaatacc tgttccccgg ggagtgccag tacgttctgg tgcaggatta ctgcggcagt   2700
aaccctggga cctttcggat cctagtgggg aataagggat gcagccaccc ctcagtgaaa   2760
```

-continued

```
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg aattttgat    3000 ggcatccaga acaatgacct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga atctccggga gaacgggtat    3420
gagtgtgagt ggcgctataa cagctgtgca cctgcctgtc aagtcacgtg tcagcaccct    3480
gagccactgg cctgccctgt gcagtgtgtg gagggctgcc atgcccactg cctccaggg    3540 aaaatcctgg atgagctttt gcagacctgc gttgaccctg aagactgtcc agtgtgtgag    3600
gtggctggcc ggcgttttgc ctcaggaaag aaagtcacct gaatcccag tgaccctgag    3660 cactgccaga tttgccactg tgatgttgtc aacctcacct gtgaagcctg ccaggagccg    3720
ggaggcctgc tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg gctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
accctgctcc tgatggccag ccaggagccc caacggatgt cccggaactt tgtccgctac    4200
gtccagggcc tgaagaagaa gaaggtcatt gtgatcccgg tgggcattgg gccccatgcc    4260
aacctcaagc agatccgcct catcgagaag caggcccctg agaacaaggc cttcgtgctg    4320
agcagtgtgg atgagctgga gcagcaaagg gacgagatcg ttagctacct ctgtgacctt    4380
gcccctgaag cccctcctcc tactctgccc cccgacatgg cacaagtcac tgtgggcccg    4440
gggctcttgg gggtttcgac cctggggccc aagaggaact ccatggttct ggatgtggcg    4500
ttcgtcctgg aaggatcgga caaaattggt gaagccgact tcaacaggag caaggagttc    4560
atggaggagg tgattcagcg gatggatgtg ggccaggaca gcatccacgt cacggtgctg    4620
cagtactcct acatggtgac tgtggagtac cccttcagcg aggcacagtc caaaggggac    4680
atcctgcagc gggtgcgaga gatccgctac cagggcggca acaggaccaa cactgggctg    4740
gccctgcggt acctctctga ccacagcttc ttggtcagcc agggtgaccg ggagcaggcg    4800
cccaacctgg tctacatggt caccggaaat cctgcctctg atgagatcaa gaggctgcct    4860
ggagacatcc aggtggtgcc cattggagtg ggccctaatg ccaacgtgca ggagctggag    4920
aggattggct ggcccaatgc ccctatcctc atccaggact ttgagacgct ccccgagag    4980 gctcctgacc tggtgctgca gaggtgctgc tccggagagg ggctgcagat ccccacccct    5040
tcccctgcac ctcgtgatga gacgctccag gatggctgtg atactcactt ctgcaaggtc    5100
aatgagagag gagagtactt ctgggagaag agggtcacag gctgcccacc ctttgatgaa    5160
```

```
cacaagtgtc tggctgaggg aggtaaaatt atgaaaattc caggcacctg ctgtgacaca    5220
tgtgaggagc ctgagtgcaa cgacatcact gccaggctgc agtatgtcaa ggtgggaagc    5280
tgtaagtctg aagtagaggt ggatatccac tactgccagg gcaaatgtgc cagcaaagcc    5340
atgtactcca ttgacatcaa cgatgtgcag gaccagtgct cctgctgctc tccgacacgg    5400
acggagccca tgcaggtggc cctgcactgc accaatggct ctgttgtgta ccatgaggtt    5460
ctcaatgcca tggagtgcaa atgctccccc aggaagtgca gcaagtga                 5508
```

```
<210> SEQ ID NO 4
<211> LENGTH: 1833
<212> TYPE: PRT
<213> ORGANISM: Homo sapiens

<400> SEQUENCE: 4
```

```
Met Ile Pro Ala Arg Phe Ala Gly Val Leu Ala Leu Ala Leu Ile
1               5                  10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320
```

```
Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
            450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735
```

-continued

```
His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
        820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr His Val Cys Asp Ala
        850                 855                 860

Thr Cys Ser Thr Ile Gly Met Ala His Tyr Leu Thr Phe Asp Gly Leu
865                 870                 875                 880

Lys Tyr Leu Phe Pro Gly Glu Cys Gln Tyr Val Leu Val Gln Asp Tyr
                885                 890                 895

Cys Gly Ser Asn Pro Gly Thr Phe Arg Ile Leu Val Gly Asn Lys Gly
                900                 905                 910

Cys Ser His Pro Ser Val Lys Cys Lys Lys Arg Val Thr Ile Leu Val
                915                 920                 925

Glu Gly Gly Glu Ile Glu Leu Phe Asp Gly Val Asn Val Lys Arg
930                 935                 940

Pro Met Lys Asp Glu Thr His Phe Glu Val Val Glu Ser Gly Arg Tyr
945                 950                 955                 960

Ile Ile Leu Leu Leu Gly Lys Ala Leu Ser Val Val Trp Asp Arg His
                965                 970                 975

Leu Ser Ile Ser Val Val Leu Lys Gln Thr Tyr Gln Glu Lys Val Cys
                980                 985                 990

Gly Leu Cys Gly Asn Phe Asp Gly Ile Gln Asn Asn Asp Leu Thr Ser
                995                 1000                1005

Ser Asn Leu Gln Val Glu Glu Asp Pro Val Asp Phe Gly Asn Ser
1010                1015                1020

Trp Lys Val Ser Ser Gln Cys Ala Asp Thr Arg Lys Val Pro Leu
1025                1030                1035

Asp Ser Ser Pro Ala Thr Cys His Asn Asn Ile Met Lys Gln Thr
1040                1045                1050

Met Val Asp Ser Ser Cys Arg Ile Leu Thr Ser Asp Val Phe Gln
1055                1060                1065

Asp Cys Asn Lys Leu Val Asp Pro Glu Pro Tyr Leu Asp Val Cys
1070                1075                1080

Ile Tyr Asp Thr Cys Ser Cys Glu Ser Ile Gly Asp Cys Ala Cys
1085                1090                1095

Phe Cys Asp Thr Ile Ala Ala Tyr Ala His Val Cys Ala Gln His
1100                1105                1110

Gly Lys Val Val Thr Trp Arg Thr Ala Thr Leu Cys Pro Gln Ser
1115                1120                1125

Cys Glu Glu Arg Asn Leu Arg Glu Asn Gly Tyr Glu Cys Glu Trp
1130                1135                1140
```

-continued

```
Arg Tyr Asn Ser Cys Ala Pro Ala Cys Gln Val Thr Cys Gln His
    1145                1150                1155
Pro Glu Pro Leu Ala Cys Pro Val Gln Cys Val Glu Gly Cys His
    1160                1165                1170
Ala His Cys Pro Pro Gly Lys Ile Leu Asp Glu Leu Leu Gln Thr
    1175                1180                1185
Cys Val Asp Pro Glu Asp Cys Pro Val Cys Glu Val Ala Gly Arg
    1190                1195                1200
Arg Phe Ala Ser Gly Lys Lys Val Thr Leu Asn Pro Ser Asp Pro
    1205                1210                1215
Glu His Cys Gln Ile Cys His Cys Asp Val Val Asn Leu Thr Cys
    1220                1225                1230
Glu Ala Cys Gln Glu Pro Gly Gly Leu Val Val Pro Pro Thr Asp
    1235                1240                1245
Ala Pro Val Ser Pro Thr Thr Leu Tyr Val Glu Asp Ile Ser Glu
    1250                1255                1260
Pro Pro Leu His Asp Phe Tyr Cys Ser Arg Leu Leu Asp Leu Val
    1265                1270                1275
Phe Leu Leu Asp Gly Ser Ser Arg Leu Ser Glu Ala Glu Phe Glu
    1280                1285                1290
Val Leu Lys Ala Phe Val Val Asp Met Met Glu Arg Leu Arg Ile
    1295                1300                1305
Ser Gln Lys Trp Val Arg Val Ala Val Val Glu Tyr His Asp Gly
    1310                1315                1320
Ser His Ala Tyr Ile Gly Leu Lys Asp Arg Lys Arg Pro Ser Glu
    1325                1330                1335
Leu Arg Arg Ile Ala Ser Gln Val Lys Tyr Ala Gly Ser Gln Val
    1340                1345                1350
Ala Ser Thr Ser Glu Val Leu Lys Tyr Thr Leu Phe Gln Ile Phe
    1355                1360                1365
Ser Lys Ile Asp Arg Pro Glu Ala Ser Arg Ile Thr Leu Leu Leu
    1370                1375                1380
Met Ala Ser Gln Glu Pro Gln Arg Met Ser Arg Asn Phe Val Arg
    1385                1390                1395
Tyr Gln Gly Leu Lys Lys Lys Lys Val Ile Val Ile Pro Val Gly
    1400                1405                1410
Ile Gly Pro His Ala Asn Leu Lys Gln Ile Arg Leu Ile Glu Lys
    1415                1420                1425
Gln Ala Pro Glu Asn Lys Ala Phe Val Leu Ser Ser Val Asp Glu
    1430                1435                1440
Leu Glu Gln Gln Arg Asp Glu Ile Val Ser Tyr Leu Cys Asp Leu
    1445                1450                1455
Ala Pro Glu Ala Pro Pro Thr Leu Pro Pro Asp Met Ala Gln
    1460                1465                1470
Val Thr Val Gly Pro Gly Leu Leu Gly Val Ser Thr Leu Gly Pro
    1475                1480                1485
Lys Arg Asn Ser Met Val Leu Asp Val Ala Phe Val Leu Glu Gly
    1490                1495                1500
Ser Asp Lys Ile Gly Glu Ala Asp Phe Asn Arg Ser Lys Glu Phe
    1505                1510                1515
Met Glu Glu Val Ile Gln Arg Met Asp Val Gly Gln Asp Ser Ile
    1520                1525                1530
```

His Val Thr Val Leu Gln Tyr Ser Tyr Met Thr Val Glu Tyr
1535                1540                1545

Pro Phe Ser Glu Ala Gln Ser Lys Gly Asp Ile Leu Gln Arg Val
1550                1555                1560

Arg Glu Ile Arg Tyr Gln Gly Gly Asn Arg Thr Asn Thr Gly Leu
1565                1570                1575

Ala Leu Arg Tyr Leu Ser Asp His Ser Phe Leu Val Ser Gln Gly
1580                1585                1590

Asp Arg Glu Gln Ala Pro Asn Leu Val Tyr Met Val Thr Gly Asn
1595                1600                1605

Pro Ala Ser Asp Glu Ile Lys Arg Leu Pro Gly Asp Ile Gln Val
1610                1615                1620

Val Pro Ile Gly Val Gly Pro Asn Ala Asn Val Gln Glu Leu Glu
1625                1630                1635

Arg Ile Gly Trp Pro Asn Ala Pro Ile Leu Ile Gln Asp Phe Glu
1640                1645                1650

Thr Leu Pro Arg Glu Ala Pro Asp Leu Val Leu Gln Arg Cys Cys
1655                1660                1665

Ser Gly Glu Gly Leu Gln Ile Pro Thr Leu Ser Pro Ala Pro Arg
1670                1675                1680

Asp Glu Thr Leu Gln Asp Gly Cys Asp Thr His Phe Cys Lys Val
1685                1690                1695

Asn Glu Arg Gly Glu Tyr Phe Trp Glu Lys Arg Val Thr Gly Cys
1700                1705                1710

Pro Pro Phe Asp Glu His Lys Cys Leu Ala Glu Gly Gly Lys Ile
1715                1720                1725

Met Lys Ile Pro Gly Thr Cys Cys Asp Thr Cys Glu Glu Pro Glu
1730                1735                1740

Cys Asn Asp Ile Thr Ala Arg Leu Gln Tyr Val Lys Val Gly Ser
1745                1750                1755

Cys Lys Ser Glu Val Glu Val Asp Ile His Tyr Cys Gln Gly Lys
1760                1765                1770

Cys Ala Ser Lys Ala Met Tyr Ser Ile Asp Ile Asn Asp Val Gln
1775                1780                1785

Asp Gln Cys Ser Cys Cys Ser Pro Thr Arg Thr Glu Pro Met Gln
1790                1795                1800

Val Ala Leu His Cys Thr Asn Gly Ser Val Val Tyr His Glu Val
1805                1810                1815

Leu Asn Ala Met Glu Cys Lys Cys Ser Pro Arg Lys Cys Ser Lys
1820                1825                1830

<210> SEQ ID NO 5
<211> LENGTH: 6075
<212> TYPE: DNA
<213> ORGANISM: Homo sapiens

<400> SEQUENCE: 5
atgattcctg ccagatttgc cggggtgctg cttgctctgg ccctcatttt gccagggacc    60
ctttgtgcag aaggaactcg cggcaggtca tccacggccc gatgcagcct ttcggaagt   120 gacttcgtca acacctttga tgggagcatg tacagctttg cgggatactg cagttacctc   180
ctggcagggg gctgccagaa acgctccttc tcgattattg ggacttccag aatggcaag   240 agagtgagcc tctccgtgta tcttggggaa tttttgaca tccatttgtt tgtcaatggt   300
accgtgacac aggggggacca aagagtctcc atgcccctatg cctccaaagg gctgtatcta   360

```
gaaactgagg ctgggtacta caagctgtcc ggtgaggcct atggctttgt ggccaggatc    420
gatggcagcg gcaactttca agtcctgctg tcagacagat acttcaacaa gacctgcggg    480
ctgtgtggca actttaacat ctttgctgaa gatgacttta tgacccaaga agggaccttg    540
acctcggacc cttatgactt tgccaactca tgggctctga gcagtggaga acagtggtgt    600
gaacgggcat ctcctcccag cagctcatgc aacatctcct ctggggaaat gcagaagggc    660
ctgtgggagc agtgccagct tctgaagagc acctcggtgt ttgcccgctg ccaccctctg    720
gtggaccccg agccttttgt ggccctgtgt gagaagactt tgtgtgagtg tgctgggggg    780
ctggagtgcg cctgccctgc cctcctggag tacgcccgga cctgtgccca ggagggaatg    840
gtgctgtacg gctggaccga ccacagcgcg tgcagcccag tgtgccctgc tggtatggag    900
tataggcagt gtgtgtcccc ttgcgccagg acctgccaga gcctgcacat caatgaaatg    960
tgtcaggagc gatgcgtgga tggctgcagc tgccctgagg acagctcct ggatgaaggc    1020 ctctgcgtgg agagcaccga gtgtccctgc gtgcattccg aaagcgcta ccctcccggc    1080 acctccctct ctcgagactg caacacctgc atttgccgaa acagccagtg gatctgcagc    1140
aatgaagaat gtccagggga gtgccttgtc acaggtcaat cacacttcaa gagctttgac    1200
aacagatact tcaccttcag tgggatctgc cagtacctgc tggcccggga ttgccaggac    1260
cactccttct ccattgtcat tgagactgtc cagtgtgctg atgaccgcga cgctgtgtgc    1320
acccgctccg tcaccgtccg gctgcctggc ctgcacaaca gccttgtgaa actgaagcat    1380
ggggcaggag ttgccatgga tggccaggac gtccagctcc ccctcctgaa aggtgacctc    1440
cgcatccagc atacagtgac ggcctccgtg cgcctcagct acgggaggga cctgcagatg    1500
gactgggatg ccgcgggag gctgctggtg aagctgtccc ccgtctatgc cgggaagacc    1560
tgcggcctgt gtgggaatta caatggcaac cagggcgacg acttccttac ccctctgggg    1620
ctggcggagc cccgggtgga ggacttcggg aacgcctgga agctgcacgg ggactgccag    1680
gacctgcaga agcagcacag cgatccctgc gccctcaacc cgcgcatgac caggttctcc    1740
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggcctgcg cggggagagg cgtgcgcgtc    1920
gcgtggcgcg agccaggccg ctgtgagctg aactgcccga aaggccaggt gtacctgcag    1980
tgcgggaccc cctgcaacct gacctgccgc tctctctctt acccggatga ggaatgcaat    2040
gaggcctgcc tggagggctg cttctgcccc ccagggctct acatggatga gaggggggac    2100
tgcgtgccca aggcccagtg ccctgttac tatgacggtg agatcttcca gccagaagac    2160
atcttctcag accatcacac catgtgctac tgtgaggatg gcttcatgca ctgtaccatg    2220
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc cccccgggca tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcaggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
```

```
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg cctgtgtgg gaattttgat     3000 ggcatccaga acaatgacct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga atctccggga gaacgggtat    3420
gagtgtgagt ggcgctataa cagctgtgca cctgcctgtc aagtcacgtg tcagcaccct    3480
gagccactgg cctgccctgt gcagtgtgtg gagggctgcc atgcccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct gaatcccag tgaccctgag     3660
```

```
gccaatatag ggcctcgtct cactcaggtg tcagtgctgc agtatggaag catcaccacc    5220
attgacgtgc catggaacgt ggtcccggag aaagcccatt tgctgagcct tgtggacgtc    5280
atgcagcggg agggaggccc cagccaaatc ggggatgcct tgggctttgc tgtgcgatac    5340
ttgacttcag aaatgcatgg tgccaggccg ggagcctcaa aggcggtggt catcctggtc    5400
acggacgtct ctgtggattc agtggatgca gcagctgatg ccgccaggtc aacagagtg    5460 acagtgttcc ctattggaat tggagatcgc tacgatgcag cccagctacg gatcttggca    5520
ggcccagcag gcgactccaa cgtggtgaag ctccagcgaa tcgaagacct ccctaccatg    5580
gtcaccttgg caattccctt cctccacaaa ctgtgctctc gtgatgagac gctccaggat    5640
ggctgtgata ctcacttctg caaggtcaat gagagaggag agtacttctg ggagaagagg    5700
gtcacaggct gcccacccct tgatgaacac aagtgtctgg ctgagggagg taaaattatg    5760
aaaattccag gcacctgctg tgacacatgt gaggagcctg agtgcaacga catcactgcc    5820
aggctgcagt atgtcaaggt gggaagctgt aagtctgaag tagaggtgga tatccactac    5880
tgccagggca aatgtgccag caaagccatg tactccattg acatcaacga tgtgcaggac    5940
cagtgctcct gctgctctcc gacacggacg gagcccatgc aggtggccct gcactgcacc    6000
aatggctctg ttgtgtacca tgaggttctc aatgccatgg agtgcaaatg ctcccccagg    6060
aagtgcagca agtga                                                     6075
```

<210> SEQ ID NO 6
<211> LENGTH: 2023
<212> TYPE: PRT
<213> ORGANISM: Homo sapiens

<400> SEQUENCE: 6

```
Met Ile Pro Ala Arg Phe Ala Gly Val Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205
```

-continued

```
Ser Cys Asn Ile Ser Ser Gly Glu Met Gln Lys Gly Leu Trp Glu Gln
210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
            245                 250                 255
Cys Ala Gly Gly Leu Glu Cys Ala Cys Pro Ala Leu Leu Glu Tyr Ala
            260                 265                 270
Arg Thr Cys Ala Gln Glu Gly Met Val Leu Tyr Gly Trp Thr Asp His
        275                 280                 285
Ser Ala Cys Ser Pro Val Cys Pro Ala Gly Met Glu Tyr Arg Gln Cys
290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
            340                 345                 350
Ser Gly Lys Arg Tyr Pro Pro Gly Thr Ser Leu Ser Arg Asp Cys Asn
        355                 360                 365
Thr Cys Ile Cys Arg Asn Ser Gln Trp Ile Cys Ser Asn Glu Glu Cys
370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
            420                 425                 430
Ala Asp Asp Arg Asp Ala Val Cys Thr Arg Ser Val Thr Val Arg Leu
        435                 440                 445
Pro Gly Leu His Asn Ser Leu Val Lys Leu Lys His Gly Ala Gly Val
450                 455                 460
Ala Met Asp Gly Gln Asp Val Gln Leu Pro Leu Leu Lys Gly Asp Leu
465                 470                 475                 480
Arg Ile Gln His Thr Val Thr Ala Ser Val Arg Leu Ser Tyr Gly Glu
                485                 490                 495
Asp Leu Gln Met Asp Trp Asp Gly Arg Gly Arg Leu Leu Val Lys Leu
            500                 505                 510
Ser Pro Val Tyr Ala Gly Lys Thr Cys Gly Leu Cys Gly Asn Tyr Asn
        515                 520                 525
Gly Asn Gln Gly Asp Asp Phe Leu Thr Pro Ser Gly Leu Ala Glu Pro
530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
                565                 570                 575
Thr Arg Phe Ser Glu Glu Ala Cys Ala Val Leu Thr Ser Pro Thr Phe
            580                 585                 590
Glu Ala Cys His Arg Ala Val Ser Pro Leu Pro Tyr Leu Arg Asn Cys
        595                 600                 605
Arg Tyr Asp Val Cys Ser Cys Ser Asp Gly Arg Glu Cys Leu Cys Gly
610                 615                 620
```

```
Ala Leu Ala Ser Tyr Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
        660                 665                 670

Ser Tyr Pro Asp Glu Glu Cys Asn Glu Ala Cys Leu Glu Gly Cys Phe
    675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
    755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Gln Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
        915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035
```

```
Leu Asp Ser Ser Pro Ala Thr Cys His Asn Asn Ile Met Lys Gln
1040                1045                1050

Thr Met Val Asp Ser Ser Cys Arg Ile Leu Thr Ser Asp Val Phe
1055                1060                1065

Gln Asp Cys Asn Lys Leu Val Asp Pro Glu Pro Tyr Leu Asp Val
1070                1075                1080

Cys Ile Tyr Asp Thr Cys Ser Cys Glu Ser Ile Gly Asp Cys Ala
1085                1090                1095

Cys Phe Cys Asp Thr Ile Ala Ala Tyr Ala His Val Cys Ala Gln
1100                1105                1110

His Gly Lys Val Val Thr Trp Arg Thr Ala Thr Leu Cys Pro Gln
1115                1120                1125

Ser Cys Glu Glu Arg Asn Leu Arg Glu Asn Gly Tyr Glu Cys Glu
1130                1135                1140

Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Thr Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
1415                1420                1425
```

-continued

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro Asp Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695

Ser Ser Ser Phe Pro Ala Ser Tyr Phe Asp Glu Met Lys Ser Phe
1700                1705                1710

Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Gln Arg Glu Gly Gly Pro Ser Gln Ile Gly Asp Ala Leu
1760                1765                1770

Gly Phe Ala Val Arg Tyr Leu Thr Ser Glu Met His Gly Ala Arg
1775                1780                1785

Pro Gly Ala Ser Lys Ala Val Val Ile Leu Val Thr Asp Val Ser
1790                1795                1800

Val Asp Ser Val Asp Ala Ala Ala Asp Ala Ala Arg Ser Asn Arg
1805                1810                1815

```
Val Thr Val Phe Pro Ile Gly Ile Gly Asp Arg Tyr Asp Ala Ala
            1820                1825                1830

Gln Leu Arg Ile Leu Ala Gly Pro Ala Gly Asp Ser Asn Val Val
        1835                1840                1845

Lys Leu Gln Arg Ile Glu Asp Leu Pro Thr Met Val Thr Leu Gly
    1850                1855                1860

Asn Ser Phe Leu His Lys Leu Cys Ser Arg Asp Glu Thr Leu Gln
1865                1870                1875

Asp Gly Cys Asp Thr His Phe Cys Lys Val Asn Glu Arg Gly Glu
    1880                1885                1890

Tyr Phe Trp Glu Lys Arg Val Thr Gly Cys Pro Pro Phe Asp Glu
        1895                1900                1905

His Lys Cys Leu Ala Glu Gly Gly Lys Ile Met Lys Ile Pro Gly
            1910                1915                1920

Thr Cys Cys Asp Thr Cys Glu Glu Pro Glu Cys Asn Asp Ile Thr
                1925                1930                1935

Ala Arg Leu Gln Tyr Val Lys Val Gly Ser Cys Lys Ser Glu Val
            1940                1945                1950

Glu Val Asp Ile His Tyr Cys Gln Gly Lys Cys Ala Ser Lys Ala
        1955                1960                1965

Met Tyr Ser Ile Asp Ile Asn Asp Val Gln Asp Gln Cys Ser Cys
    1970                1975                1980

Cys Ser Pro Thr Arg Thr Glu Pro Met Gln Val Ala Leu His Cys
1985                1990                1995

Thr Asn Gly Ser Val Val Tyr His Glu Val Leu Asn Ala Met Glu
    2000                2005                2010

Cys Lys Cys Ser Pro Arg Lys Cys Ser Lys
2015                2020

<210> SEQ ID NO 7
<211> LENGTH: 4329
<212> TYPE: DNA
<213> ORGANISM: Homo sapiens

<400> SEQUENCE: 7
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt ccattcaac     180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
```

```
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg ggaagttgg agacacactg    1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat ggccctctc ctcatctgct acaaagaatc tgtagatcaa    1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccttc aaacacaaa    2040
atggtctatg aagacacact caccctattc ccattctcag agaaactgt cttcatgtcg     2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca tgccattga accaagaata    2280
actcgtacta ctcttcagtc agatcaagag gaaattgact atgatgatac catatcagtt   2340
gaaatgaaga aggaagattt tgacatttat gatgaggatg aaaatcagag ccccgcagc    2400
tttcaaaaga aaacacgaca ctattttatt gctgcagtgg agaggctctg ggattatggg   2460
atgagtagct cccacacatg tctaagaaac agggctcaga gtggcagtgt ccctcagttc   2520
aagaaagttg ttttccagga atttactgat ggctcctta ctcagccctt ataccgtgga    2580
gaactaaatg aacatttggg actcctgggg ccatatataa agcagaagt tgaagataat    2640
atcatggtaa ctttcagaaa tcaggcctct cgtccctatt ccttctattc tagccttatt   2700
tcttatgagg aagatcagag gcaaggagca gaacctagaa aaaactttgt caagcctaat   2760
gaaaccaaaa cttactttg gaaagtgcaa catcatatgg cacccactaa agatgagttt    2820
gactgcaaag cctgggctta tttctctgat gttgacctgg aaaagatgt gcactcaggc    2880
ctgattggac cccttctggt ctgccacact aacacactga accctgctca tgggagacaa   2940
gtgacagtac aggaatttgc tctgtttttc accatctttg atgagaccaa agctggtac    3000
ttcactgaaa atatgaaag aaactgcagg gctccctgca atatccagat ggaagatccc   3060
acttttaaag agaattatcg cttccatgca atcaatggct acataatgga tacactacct   3120
ggcttagtaa tggctcagga tcaaaggatt cgatggtatc tgctcagcat gggcagcaat   3180
gaaaacatcc attctattca tttcagtgga catgtgttca ctgtacgaaa aaagaggag    3240
tataaaatgg cactgtacaa tctctatcca ggtgttttg agacagtgga aatgttacca   3300
```

-continued

```
tccaaagctg gaatttggcg ggtggaatgc cttattggcg agcatctaca tgctgggatg    3360
agcacacttt ttctggtgta cagcaataag tgtcagactc ccctgggaat ggcttctgga    3420
cacattagag attttcagat tacagcttca ggacaatatg gacagtgggc cccaaagctg    3480
gccagacttc attattccgg atcaatcaat gcctggagca ccaaggagcc ctttttcttgg   3540
atcaaggtgg atctgttggc accaatgatt attcacggca tcaagaccca gggtgcccgt    3600
cagaagttct ccagcctcta catctctcag tttatcatca tgtatagtct tgatgggaag    3660
aagtggcaga cttatcgagg aaattccact ggaaccttaa tggtcttctt tggcaatgtg    3720
gattcatctg gataaaaaca caatattttt aaccctccaa ttattgctcg atacatccgt    3780
ttgcacccaa ctcattatag cattcgcagc actcttcgca tggagtggat gggctgtgat    3840
ttaaatagtt gcagcatgcc attgggaatg gagagtaaag caatatcaga tgcacagatt    3900
actgcttcat cctactttac caatatgttt gccacctggt ctccttcaaa agctcgactt    3960
cacctccaag ggaggagtaa tgcctggaga cctcaggtga ataatccaaa agagtggctg    4020
caagtggact tccagaagac aatgaaagtc acaggagtaa ctactcaggg agtaaaatct    4080
ctgcttacca gcatgtatgt gaaggagttc ctcatctcca gcagtcaaga tggccatcag    4140
tggactctct tttttcagaa tggcaaagta aaggttttc agggaaatca agactccttc    4200
acacctgtgg tgaactctct agacccaccg ttactgactc gctaccttcg aattcccccc   4260
cagagttggg tgcaccagat tgccctgagg atggaggttc tgggctgcga ggcacaggac    4320
ctctactga                                                             4329
```

<210> SEQ ID NO 8
<211> LENGTH: 1442
<212> TYPE: PRT
<213> ORGANISM: Homo sapiens

<400> SEQUENCE: 8

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190
```

```
Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605
```

```
Asn Ile Gln Arg Phe Leu Pro Asn Pro Ala Gly Val Gln Leu Glu Asp
610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ile Thr Arg Thr Thr Leu Gln Ser Asp
        755                 760                 765
Gln Glu Glu Ile Asp Tyr Asp Asp Thr Ile Ser Val Glu Met Lys Lys
770                 775                 780
Glu Asp Phe Asp Ile Tyr Asp Glu Asp Glu Asn Gln Ser Pro Arg Ser
785                 790                 795                 800
Phe Gln Lys Lys Thr Arg His Tyr Phe Ile Ala Ala Val Glu Arg Leu
                805                 810                 815
Trp Asp Tyr Gly Met Ser Ser Pro His Val Leu Arg Asn Arg Ala
            820                 825                 830
Gln Ser Gly Ser Val Pro Gln Phe Lys Lys Val Val Phe Gln Glu Phe
        835                 840                 845
Thr Asp Gly Ser Phe Thr Gln Pro Leu Tyr Arg Gly Glu Leu Asn Glu
850                 855                 860
His Leu Gly Leu Leu Gly Pro Tyr Ile Arg Ala Glu Val Glu Asp Asn
865                 870                 875                 880
Ile Met Val Thr Phe Arg Asn Gln Ala Ser Arg Pro Tyr Ser Phe Tyr
                885                 890                 895
Ser Ser Leu Ile Ser Tyr Glu Glu Asp Gln Arg Gln Gly Ala Glu Pro
            900                 905                 910
Arg Lys Asn Phe Val Lys Pro Asn Glu Thr Lys Thr Tyr Phe Trp Lys
        915                 920                 925
Val Gln His His Met Ala Pro Thr Lys Asp Glu Phe Asp Cys Lys Ala
930                 935                 940
Trp Ala Tyr Phe Ser Asp Val Asp Leu Glu Lys Asp Val His Ser Gly
945                 950                 955                 960
Leu Ile Gly Pro Leu Leu Val Cys His Thr Asn Thr Leu Asn Pro Ala
                965                 970                 975
His Gly Arg Gln Val Thr Val Gln Glu Phe Ala Leu Phe Phe Thr Ile
            980                 985                 990
Phe Asp Glu Thr Lys Ser Trp Tyr Phe Thr Glu Asn Met Glu Arg Asn
        995                 1000                1005
Cys Arg Ala Pro Cys Asn Ile Gln Met Glu Asp Pro Thr Phe Lys
    1010                1015                1020
```

```
Glu Asn Tyr Arg Phe His Ala Ile Asn Gly Tyr Ile Met Asp Thr
1025                1030                1035

Leu Pro Gly Leu Val Met Ala Gln Asp Gln Arg Ile Arg Trp Tyr
1040                1045                1050

Leu Leu Ser Met Gly Ser Asn Glu Asn Ile His Ser Ile His Phe
1055                1060                1065

Ser Gly His Val Phe Thr Val Arg Lys Lys Glu Glu Tyr Lys Met
1070                1075                1080

Ala Leu Tyr Asn Leu Tyr Pro Gly Val Phe Glu Thr Val Glu Met
1085                1090                1095

Leu Pro Ser Lys Ala Gly Ile Trp Arg Val Glu Cys Leu Ile Gly
1100                1105                1110

Glu His Leu His Ala Gly Met Ser Thr Leu Phe Leu Val Tyr Ser
1115                1120                1125

Asn Lys Cys Gln Thr Pro Leu Gly Met Ala Ser Gly His Ile Arg
1130                1135                1140

Asp Phe Gln Ile Thr Ala Ser Gly Gln Tyr Gly Gln Trp Ala Pro
1145                1150                1155

Lys Leu Ala Arg Leu His Tyr Ser Gly Ser Ile Asn Ala Trp Ser
1160                1165                1170

Thr Lys Glu Pro Phe Ser Trp Ile Lys Val Asp Leu Leu Ala Pro
1175                1180                1185

Met Ile Ile His Gly Ile Lys Thr Gln Gly Ala Arg Gln Lys Phe
1190                1195                1200

Ser Ser Leu Tyr Ile Ser Gln Phe Ile Ile Met Tyr Ser Leu Asp
1205                1210                1215

Gly Lys Lys Trp Gln Thr Tyr Arg Gly Asn Ser Thr Gly Thr Leu
1220                1225                1230

Met Val Phe Phe Gly Asn Val Asp Ser Ser Gly Ile Lys His Asn
1235                1240                1245

Ile Phe Asn Pro Pro Ile Ile Ala Arg Tyr Ile Arg Leu His Pro
1250                1255                1260

Thr His Tyr Ser Ile Arg Ser Thr Leu Arg Met Glu Trp Met Gly
1265                1270                1275

Cys Asp Leu Asn Ser Cys Ser Met Pro Leu Gly Met Glu Ser Lys
1280                1285                1290

Ala Ile Ser Asp Ala Gln Ile Thr Ala Ser Ser Tyr Phe Thr Asn
1295                1300                1305

Met Phe Ala Thr Trp Ser Pro Ser Lys Ala Arg Leu His Leu Gln
1310                1315                1320

Gly Arg Ser Asn Ala Trp Arg Pro Gln Val Asn Asn Pro Lys Glu
1325                1330                1335

Trp Leu Gln Val Asp Phe Gln Lys Thr Met Lys Val Thr Gly Val
1340                1345                1350

Thr Thr Gln Gly Val Lys Ser Leu Leu Thr Ser Met Tyr Val Lys
1355                1360                1365

Glu Phe Leu Ile Ser Ser Ser Gln Asp Gly His Gln Trp Thr Leu
1370                1375                1380

Phe Phe Gln Asn Gly Lys Val Lys Val Phe Gln Gly Asn Gln Asp
1385                1390                1395

Ser Phe Thr Pro Val Val Asn Ser Leu Asp Pro Pro Leu Leu Thr
1400                1405                1410
```

Arg Tyr Leu Arg Ile His Pro Gln Ser Trp Val His Gln Ile Ala
    1415                1420                1425

Leu Arg Met Glu Val Leu Gly Cys Glu Ala Gln Asp Leu Tyr
    1430                1435                1440

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gaaccgaagc tggtacct                                              18

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
gacaggaggg gcattaaatt gcttttgcct                                 30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
tttaatgccc caccagtctt gaaacgccat                                 30

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
atgctcgcca ataaggcatt cca                                        23

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
cgtgatgaga cgctccag                                              18

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ttttctggtg tcagcacact g                                          21

```
<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
aggtgcaggg gagagggt                                                 18

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
agagcacagt ttgtggag                                                 18

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
cgtgatgaga cgctccag                                                 18

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ttttctggtg tcagcacact g                                             21

<210> SEQ ID NO 19
<211> LENGTH: 17
<212> TYPE: DNA
<213> ORGANISM: Artificial Sequence
<220> FEATURE:
<223> OTHER INFORMATION: Primer

<400> SEQUENCE: 19
caggtgcagg ggagagg                                                  17
```

RECOMBINANT EXPRESSION VECTOR SYSTEM FOR VARIANTS OF COAGULATION FACTOR VIII AND VON WILLEBRAND FACTOR

CROSS-REFERENCE TO RELATED APPLICATION

This application is a division of U.S. patent application Ser. No. 12/200,928 filed on Aug. 28, 2008. U.S. Ser. No. 12/200,928 claims the benefit of Korean Patent Application No. 10-20080019392, filed on Feb. 29, 2008, in the Korean Intellectual Property Office. The disclosures of which are incorporated herein in their entirety by reference.

SEQUENCE LISTING

The instant application contains a Sequence Listing which has been submitted in ASCII format via EFS-Web and is hereby incorporated by reference in its entirety. Said ASCII copy, created on May 30, 2014, is named 88315DIV50498_ST25.txt and is 84,678 bytes in size.

BACKGROUND OF THE INVENTION

1. Field of the Invention

The present invention relates to an expression vector system for variants of coagulation Factor VIII (FVIII) and von Willebrand Factor (vWF), more particularly to mutant vWF the size of which is significantly reduced by deleting exons but which has remarkably increased FVIII stabilizing and activating efficiency, and an expression vector system useful for the treatment of hemophilia which is capable of expressing the same along with FVIII.

2. Description of the Related Art

Hemophilia A is a hereditary, X chromosome-linked blood clotting disorder caused by a deficiency in FVIII. Symptoms include frequent bleeding in muscles, bones, digestive and urinary tracts, etc. accompanied by swelling and pain. Current treatment is based on regular supplementation of FVIII. This requires a lifelong treatment, giving troubles in daily lives and economic burdens. Further, there is a high risk of secondary infection during its administration.

FVIII is a large glycoprotein of 180 Kb, and consists of A1-A2-B-A3-C1-C2 domains. The FVIII gene is located on the X chromosome, and its synthesis is carried out mostly in the liver. Until now, there have been a lot of researches to transducer FVIII, but there were many difficulties because its size was too large, or the transduced FVIII gene was not expressed or secreted well. The B domain of FVIII consists of a large exon and its asparagine, serine and threonine residues are highly glycosylated. According to recent functional studies, the domain is not essential in procoagulant activity, and the deletion thereof does not affect the function of FVIII. When B-domain deleted FVIII (BDD-FVIII) was expressed in cells, the problems of unstable FVIII mRNA structure and interaction with ER chaperones were overcome and a lot of FVIII mRNA could be attained. Of the BDD-FVIII, a variant with 226 amino acids at the N-terminal with 6 consensus site for N-linked glycosylation exhibited significantly increased FVIII secretion.

In genetic treatment of hemophilia A, the target cell is bone marrow cells, especially stem cells or progenitor cells. Lentivirus-based vectors are used to transfer the gene. After infection into cells, these vectors insert the gene into the chromosome of the infected cell, thereby enabling stable and consistent expression. Other viruses such as Moloney murine leukemia virus could not be used to infect stem cells or progenitor cells, because they infect only dividing cells. And, although adenovirus produces a large amount of expressed proteins, a consistent expression was impossible because the gene is diluted as the differentiation continues.

Accordingly, a safe and consistent way of transducing FVIII is necessary, and the development thereof is needed. Lentiviral vectors can infect nearly all non-dividing cells, as well as dividing cells, and provide stable expression for a long period of time because they are inserted in the cell chromosome after the infection. Thus, lentivirus-based vectors for expression of FVIII may be useful for gene therapy.

vWF plays an important role in activating FVIII during blood coagulation. vWF is a blood glycoprotein which binds to FVIII thereby preventing it from being degraded in the blood. Besides, it plays a major role in blood coagulation by binding to collagen or platelet when endothelial cells are injured. vWF consists of D'-D3-A1-A2-A3-D4-B1-B2-B3-C1-C2 domains, and the D'-D3 domain binds to FVIII. vWF is a 250 kDa-sized protein and its gene is about 9 Kb in size. Accordingly, it is impossible to insert vWF in a lentiviral vector to help the function of FVIII. Through researches on the essential part in the vWF domains with respect to activation of FVIII, the inventors of the present invention found out that the portion of the vWF gene up to exon 32 functions most efficiently. Based on this finding, we inserted FVIII, an internal ribosome entry site (IRES) and vWF in a lentivirus-based vector. The resultant viral vector expresses the proteins gag-pol, env, tat and rev required for lentivirus, thereby expressing FVIII and vWF upon infection of cells. This attempt has never been made and is valued very highly for gene therapies and hemophilia researches in the future.

SUMMARY OF THE INVENTION

Accordingly, the present invention is directed to provide mutant von Willebrand Factor (vWF) the size of which is significantly reduced by deleting exons but which has remarkably increased coagulation Factor VIII (FVIII) stabilizing and activating efficiency.

The present invention is also directed to provide a vector which expresses FVIII and vWF consistently and stably in cells.

Through expression of the factors, the present invention aims at providing a successful gene therapy for hemophilia A. The present invention is distinguished from other existing inventions in that not only FVIII but also vWF, which is essential for the function thereof, is expressed together.

To prove the effect of the present invention, VSV-G pseudotyped lentivirus expressing FVIII and vWF was produced using a lentivirus-based vector and transfected into various cells. Then, the activity of FVIII expressed in the cells was measured. It was determined by quantitating the level of activation of Factor X by FVIII and activated Factor IX.

In an aspect, the present invention provides mutant vWF (vWF23) having an amino acid sequence of SEQ ID NO: 2 in which exons 24-46 of vWF are deleted.

In another aspect, the present invention provides a mutant vWF23 gene having a base sequence encoding for a protein having an amino acid sequence of SEQ ID NO: 2. Preferably, the gene may have a base sequence of SEQ ID NO: 1.

In another aspect, the present invention provides mutant vWF (vWF28) having an amino acid sequence of SEQ ID NO: 4 in which exons 29-46 of vWF are deleted.

In another aspect, the present invention provides a mutant vWF28 gene having a base sequence encoding for a protein having an amino acid sequence of SEQ ID NO: 4. Preferably, the gene may have a base sequence of SEQ ID NO: 3.

In another aspect, the present invention provides mutant vWF (vWF32) having an amino acid sequence of SEQ ID NO: 6 in which exons 33-48 of vWF are deleted.

In another aspect, the present invention provides a mutant vWF32 gene having a base sequence encoding for a protein having an amino acid sequence of SEQ ID NO: 6. Preferably, the gene may have a base sequence of SEQ ID NO: 5.

In another aspect, the present invention provides an animal cell expression vector comprising a gene encoding for the mutant vWF (vWF23, vWF28 or vWF32).

In the present invention, the animal cell expression vector may be any non-viral (plasmid or liposome) or viral vector capable of delivering and expressing the gene in an animal cell. Preferably, it may be a viral vector such as retroviral vector, lentiviral vector, adenoviral vector and adeno-associated viral vector. More preferably, it may be a lentiviral vector. In FIG. 12, lentiviral vectors pvEx23, pvEx28 and pvEx32, which express the vWF23, vWF28 and vWF32, respectively, are disclosed.

In the present invention, the animal cell expression vector may further comprise a gene encoding for B-domain-deleted human FVIII. In this case, the two effective ingredients for the treatment of hemophilia may be expressed using a single vector.

In the present invention, the B-domain-deleted human FVIII may preferably have an amino acid sequence of SEQ ID NO: 8, and its gene may have a base sequence of SEQ ID NO: 7.

In the present invention, the animal cell expression vector capable of expressing both the mutant vWF (vWF23, vWF28 or vWF32) and the B-domain-deleted human FVIII may be any non-viral (plasmid or liposome) or viral vector. Preferably, it may be a viral vector such as retroviral vector, lentiviral vector, adenoviral vector and adeno-associated viral vector. More preferably, it may be a lentiviral vector. In FIG. 13, a pvBDD.FVIII.ires.vWex32 lentiviral vector in which the two genes are linked by an internal ribosome entry site (IRES) is disclosed as a bicistronic expression system.

In another aspect, the present invention provides lentiviral particles packaged by transfecting the lentiviral vector capable of expressing the mutant vWF or B-domain-deleted human FVIII in a packaging cell.

In the present invention, the packaging cell may be any one capable of packaging the lentiviral vector to form lentiviral particles, such as 293T cells and HT1080 cells. Preferably, 293T cells may be used.

In the present invention, the lentiviral vector is cotransfected with pGag-pol, pRev, pTat and pVSV-G in order to form the lentiviral particles. In the example that follows, a split gene expression system was used for safe production of viruses. That is, only the factors gag-pol, tat, rev and VSV-G essential for the production of viruses were expressed, but they were delivered through different vectors in order to reduce the possibility of recombination.

In another aspect, the present invention provides a pharmaceutical composition for the treatment and prevention of hemophilia comprising the animal cell expression vector or the mutant vWF and B-domain-deleted human FVIII expressed therefrom as an active ingredient.

In another aspect, the present invention provides a pharmaceutical composition for the treatment and prevention of hemophilia comprising the lentiviral particles as an active ingredient.

Hereinafter, the present invention will be described in more detail.

The inventors of the present invention developed a lentiviral-based expression vector system which expresses coagulation Factor VIII (FVIII) and mutant von Willebrand factor (vWF) at the same time. Specifically, we confirmed the expression and activation of FVIII by the lentiviral-based system and elucidated the domain of vWF essential for the activation of FVIII.

The FVIII use in the present invention is a B-domain-deleted FVIII (BDD-FVIII) for increasing the secretion of FVIII. The B domain of FVIII consists of one large exon and its asparagine, serine and threonine residues are highly glycosylated. According to recent functional studies, the domain is not essential in procoagulant activity, and the deletion thereof does not affect the function of FVIII. When BDD-FVIII was expressed in cells, the problems of unstable FVIII mRNA structure and interaction with ER chaperones were overcome and a lot of FVIII mRNA could be attained.

Of the BDD-FVIII, a variant with 226 amino acids at the N-terminal with 6 consensus site for N-linked glycosylation exhibited significantly increased FVIII secretion. Lentiviral vectors can infect nearly all non-dividing cells, as well as dividing cells, and provide stable expression for a long period of time because they are inserted in the cell chromosome after the infection. Thus, lentivirus-based vectors for expression of FVIII may be useful for gene therapy.

The mutant vWF of the present invention has some of its entire exons deleted, and comprises only up to D1-D2-D'-D3 domains (vWF23), D1-D2-D'-D3-A1 domains (vWF28), or D1-D2-D'-D3-A1-A2 domains (vWF32). These domains bind to FVIII, to FVIII and platelet GP1 b, or to FVIII, platelet GP1 b and collagen, respectively.

In order to maximize the FVIII activity, expression of vWF is required. It protects FVIII from deactivating factors such as thrombin, and helps the FVIII to have a stable structure. However, when FVIII and full-length vWF are expressed together outside cells, they co-localize in the cells, thereby resulting in inhibited secretion of FVIII. Accordingly, a mutant vWF is desired which maximizes the function of FVIII and comprises only the portion not inhibiting FVIII secretion.

Different mammalian expression vectors may be used to deliver FVIII and vWF. But, lentiviral-based vectors are preferred for the cells to which the delivery of gene is not easy, for example, stem cells, hematopoietic progenitor cells, and the like. However, lentiviral-based vectors have a size limit for the expressed genes. BDD.FVIII has a size of 4.4 Kb, whereas vWF has a size of 5.6 Kb up to the A2 domain. Accordingly, the gene can be expressed with no significant loss in the viral titer. Further, in order to increase viral titer, it is possible to pseudotype the envelope protein of lentivirus with VSV-G and then concentrate the virus.

The animal cell expression vector of the present invention may include a promoter derived from eukaryotic or prokaryotic cells that can induce transcription of foreign genes in animal cells. The promoter may include control elements for enhancement or repression of transcription. Suitable promoters may include cytomegalovirus promoter (pCMV), Rous sarcoma virus long terminal repeat promoter (pRSV), and SP6, T3 or T7 promoters. Enhancer sequences upstream from the promoter or terminator sequences downstream of the coding region may be optionally included in the vector of the present invention in order to facilitate expression. The vector of the present invention may further contain additional nucleotide sequences such as a polyadenylation sequence, a localization sequence or a signal sequence, sufficient to permit a cell to efficiently and effectively process the protein expressed by the nucleic acid of the vector. Examples of preferred polyadenylation sequences are SV40 early region polyadenylation site [C. V. Hall et al., *J. Molec. App. Genet.* 2, 101(1983)] and SV40 late region polyadenylation site [S. Carswell and J. C. Alwine, *Mol. Cell Biol.* 9, 4248(1989)]. Such additional sequences are inserted into the vector such that they are operably linked with the promoter sequence, if transcription is desired, or additionally with the initiation and processing sequences, if translation and processing are desired. Alternatively, the inserted sequences may be placed at any position in the vector. The term "operably linked" is used to describe a linkage between a gene sequence and a promoter or other regulatory or processing sequence such that the transcription of the a gene sequence is directed by an operably linked promoter sequence, the translation of the gene sequence is directed by an operably linked translational regulatory sequence, and the post-translational processing of the gene sequence is directed by an operably linked processing sequence.

Standard techniques for the construction of the vector of the present invention are well-known to those skilled in the art and can be found in such references as Sambrook et al., Molecular Cloning: A Laboratory Manual 2nd Ed. (Cold Spring Harbor, N.Y., 1989). A variety of strategies are available for ligating DNA fragments, the choice of which depends on the nature of the terminal of the DNA fragments and can be readily made by those skilled in the art.

Examples of the lentivirus that can be used in the present invention may include HIV-1 and HIV-2, SIV, FIV, BLV, EIAV, CEV and visna viruses. Particularly, HIV and SIV are desired for gene therapy. HIV-1 (human immunodeficiency virus type 1) is a lentivirus belonging to the retrovirus family. Like other members of the family, HIV can infect non-dividing cells. This makes lentiviruses a good candidate vector for gene therapy.

HIV-1-based vectors are the most frequently used as gene delivery vehicles due to their ability to infect dividing and non-dividing cells with their cytoplasmic and nuclear entry proteins (Kohn, 2001, *J. Intern. Med.* 249, 379-390). This ability is frequently attributed to various features of the vectors, including the nuclear localization signals in multiple virion proteins and the central polypurine tract that generates a triple stranded DNA flap' in the reverse-transcribed genome. As a consequence of these features, bioengineered HIV-1 is capable of infecting hematopoietic progenitor cells very efficiently at fairly low MOIs (Park and Choi, 2004, *Mol. Cells* 17, 297-303). The primary concern with regard to the use of lentiviral vectors as tools for gene therapy is that the transfer vector is derived from HIV-1. However, all of the viral components required for viral replication were deleted in the viral vectors utilized in the present study and the transfer vector ultimately harbored less than 5% of the HIV-1 genome. Another barrier encountered when using lentiviral vectors is restriction on the size of the transferred gene. vWF comprises 52 exons with a cDNA size of approximately 9 Kb, which exceeds the size limit of the majority of lentiviral vectors. In this report we successfully forced vWF cDNA into a lentiviral vector (FIGS. 1 and 2). In the preparation and production of the lentivirus, we substituted the env of HIV-1 with the VSV-G protein. VSV-G mediates viral entry into cells via membrane fusion rather than a specific cell surface receptor protein, resulting in a significant broadening of the host range (Hofmann et al., 1999, *J. Virol.* 12, 10010-10018). More importantly, it confers structural stability during ultracentrifugation, enabling concentration of the virus to high titers with no significant loss of infectivity (Burns et al., 1993; Hofmann et al., 1999). By exploiting these features of VSV-G, we successfully produced and concentrated vEx52, resulting in six fold higher transduction efficiency with only $\frac{1}{100}$th of the volume of lentiviral supernatant (FIG. 3). These results were FACS (Fluorescence-activated cell sorting) analyzed and clearly observed under fluorescence light: significantly greater quantities of eGFP were observed in the cells transduced with the concentrated vEx52 than with the non-concentrated vEx52 (FIG. 4). Recent work by De Meyer et al. involved incorporation of a long vWF cDNA into a lentiviral vector and transduction of blood-outgrowth endothelial cells (BOECs) from von Willebrand disease type 3 dogs to develop gene therapy with type 3 VWD (De Meyer et al., 2006, *Blood* 107, 4728-4736). However, concentrating low titers of virus may not prove to be ideal for actual application in the treatment of hemophilia A as it requires additional time-consuming and laborious procedures. Therefore, we attempted to reduce the size of the vWF cDNA insert in the lentiviral vector. We deleted domains of vWF leaving only minimal regions for interactions between vWF and FVIII. The mature vWF consists of the D'-D3-A1-A2-A3-D4-B1-B2-B3-C1-C2 domains. FVIII binds to the D'-D3 domain, and the AI domain binds to platelet glycoprotein Ib, heparin, and collagen. This facilitates the aggregation of platelets and also aids in adhesion to sites of vascular injury. The vWF gene is located on chromosome 12 and comprises 52 exons with 178,000 bases. We deleted exons 24-46 to create pRex23 and pvEx23, thus retaining only the region that binds to FVIII. FVIII binds to vWF within the 272 amino acid residues located at its amino terminus (Sadler, 1998).

We also constructed pRex28 and pvEx28, in which exons 29-46 are deleted, thereby leaving the platelet binding sites in addition to the FVIII binding region. The platelet binding site on vWF is located within the A1 domain (Sadler, 1998). When pvEx23, pvEx28 and pvEx52 were packaged into lentiviruses, virus production from pvEx23 and pvEx28 was significantly greater than from pvEx52. Generally, the viral titer of non-concentrated vEx52 was $2 \times 10^4$ to $4 \times 10^4$ particles/ml (FIG. 3), whereas the titers of vEx23 and vEx28 were between $1 \times 10^5$ and $3 \times 10^5$ particles/ml (FIG. 5). The transduction efficiencies of the three viruses can be compared from the histograms in FIGS. 3 and 5. When 500 µl of vEx23, vEx28, and vEx52 was used to transduce Jurkat cells, 35.02%, 26.30% and 4.64% of the cells, respectively, were positive for eGFP. Therefore, we were able to improve viral titers and transduction efficiencies by deleting the domains within vWF that are less important for the interaction with FVIII, thus reducing the packaging size. When pRex23, pRex28 and pRex52 were transfected into 293T cells and functional FVIII was measured in the supernatants, pRex23 and pRex28 had lower FVIII activity than observed with the full-length vWF, pRex52. However, using the viral system, the supernatants from the cells transduced with vEx28 had higher secreted BDD.FVIII activity than those from vEx52 (FIG. 6). This may be because the large size of the full-length vWF limits the efficiency its packaging and expression. While we cannot decide whether the expression of FVIII was altered by vWF, vEx28 increased the secreted level of expressed FVIII in the supernatants, and this effect is most likely attributable to protection of the conformation of BDD.FVIII. This is consistent with the observation that more FVIII activity was detected in cells when vWF was present (Kaufman et al., 1997, *Blood* 8, S3-14). Another indication that vWF stabilizes FVIII is the fact that the FVIII was degraded rapidly in the absence of vWF (Over et al., 1978, *J. Clin. Invest.* 62, 223234), whereas it was cleared more slowly in the presence of vWF (Tuddenham et al., 1982, *Br. J. Haematol.* 52, 259-267). With greater insight into the nature of vWF and FVIII, the two proteins may be engineered to provide a powerful genetic tool for correcting FVIII-deficient cells.

Pharmaceutical formulations of the present invention include those suitable for parenteral (e.g., subcutaneous, intradermal, intramuscular, intravenous and intra-arterial), oral or inhalation administration. Alternatively, pharmaceutical formulations of the present invention may be suitable for administration to the mucous membranes of a subject (e.g., intranasal administration). The formulations may be conventionally prepared in unit dosage form and may be prepared by any of the methods well known in the art.

The dosage of the pharmaceutical formulations of the present invention may vary depending on the formulation type, administration method, age, body weight and sex of the subject, severity of disease, diet, administration time, administration route, rate of excretion, response sensitivity, or the like. A skilled physician will readily determine a dosage effective for the desired treatment. In general, the pharmaceutical composition of the present invention is administered with a unit dosage of $10^3$-$10^7$ viral particles or 0.001-100 mg/kg of protein.

BRIEF DESCRIPTION OF THE DRAWINGS

The above and other features and advantages of the present invention will become more apparent by describing in detail exemplary embodiments thereof with reference to the attached drawings in.

DETAILED DESCRIPTION OF THE INVENTION

Hereinafter, the present invention will be described in more detail through examples. However, the following examples are only for the illustration of the present invention and the scope of the present invention is not to be construed as limited by them.

Example 1

Construction of Vectors

Plasmid pRF8 was obtained by cloning full length FVIII cDNA (ATCC® Accession No. 40086) into Not1 site of a modified pREP7 vector (Invitrogen™, USA) using a linker. Then, in order to delete most of B-domain, the upstream 5' region of B-domain was amplified by PCR using primers, 5'-GAACCGAAGCTGGTACCT-3' (SEQ ID NO.: 9) and 5'-GACAGGAGGGGCATTAAATTGCTTTTGCCT-3' (SEQ ID NO.: 10), and the downstream 3' region was amplified using primers, 5'-TTTAATGCCCCACCAGTCT-TGAAACGCCAT-3' (SEQ ID NO.: 11) and 5'-ATGCTCGC-CAATAAGGCATTCCA-3' (SEQ ID NO.: 12). Then, the amplified products were denatured with heat and renatured to obtain the product. The resulting product was cleaved by Kpn1 and Bgl1 and sub-cloned into Kpn1-Bgl1 of pRF8 plasmid to produce pREP7-BDD.FVIII in which B-domain-deleted (BDD) FVIII cDNA was inserted under the RSV 3' LTR control of pREP7 (Invitrogen™, USA) (see The Journal of Gene Medicine, Volume 6, Issue 7, Pages 760-768). We used the pREP7-BDD.FVII from Subrata Banerjee, an author of the thesis. Besides, pRex52 plasmid was obtained by cloning full length vWF cDNA (ATCC® #59126) into Not1 site of a modified pREP7 vector (Invitrogen™, USA) using a linker as described above.

pHIvec2.GFP obtained from Joseph Sodroski, an author of Journal of Virology, December 1999, p. 10020-10028, was used as a Lentivirus backbone (transfer vector) in the invention. The pHIvec2.GFP was prepared by deleting env and vpu sequences from v653 rtatpC virus, maintaining Rev-responsive element, and inserting eGFP gene (Clontech, USA) after IRES. The vector map of pHIvec2.GFP is the same with a vWF gene-deleted form of FIG. 1.

Figure 9:
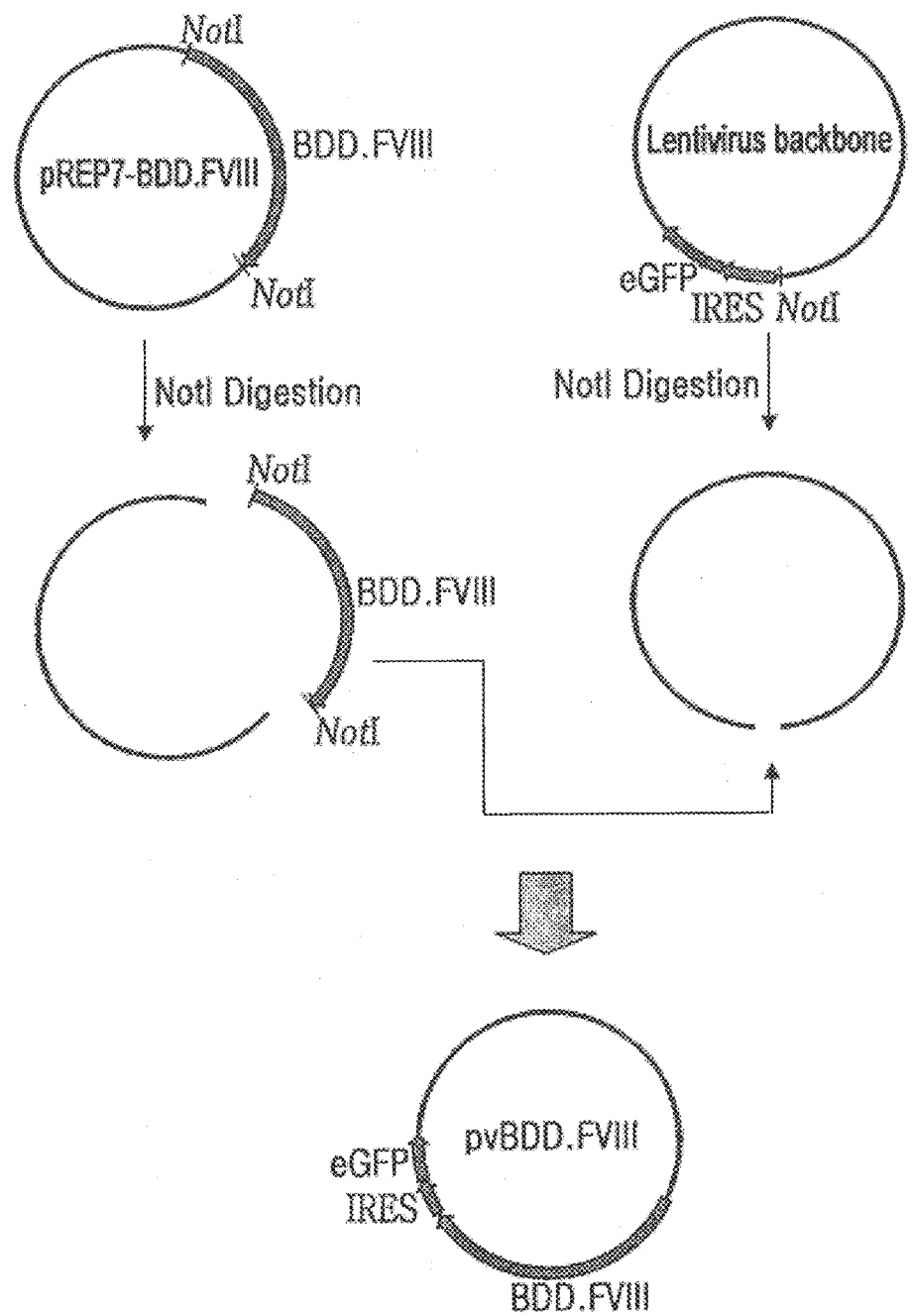
FIG. 9 illustrates a process of manufacturing a lentiviral vector comprising a B-domain-deleted FVIII gene according to an embodiment of the present invention.

To manufacture a Lentivirus vector comprising B-domain-deleted FVIII gene, cDNA of BDD.FVIII (B-Domain-Deleted Coagulation Factor VIII) was obtain from the pREP7-BDD.FVIII using Not1. The cDNA was inserted into the lentivirus backbone using the same enzyme to produce pvB-DD.FVIII. This process of manufacturing is represented in FIG. 9. In detail, pRep7-BDD.FVIII and lentivirus backbone were digested by Not1 and the BDD.FVIII fragments from pREP7-BDD.FVIII were ligated in Not1 site of lentivirus backbone.

Figure 1:
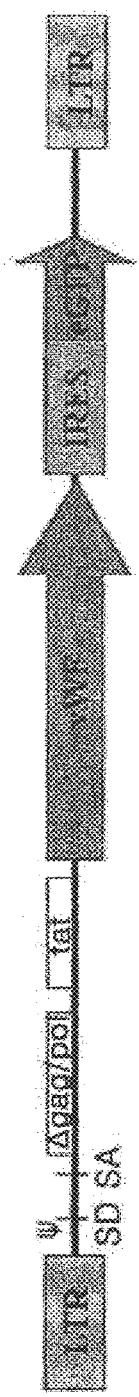
FIG. 1 schematically represents the packaging constructs comprising a mutant von Willebrand Factor (vWF) gene according to an embodiment of the present invention.
Figure 10:
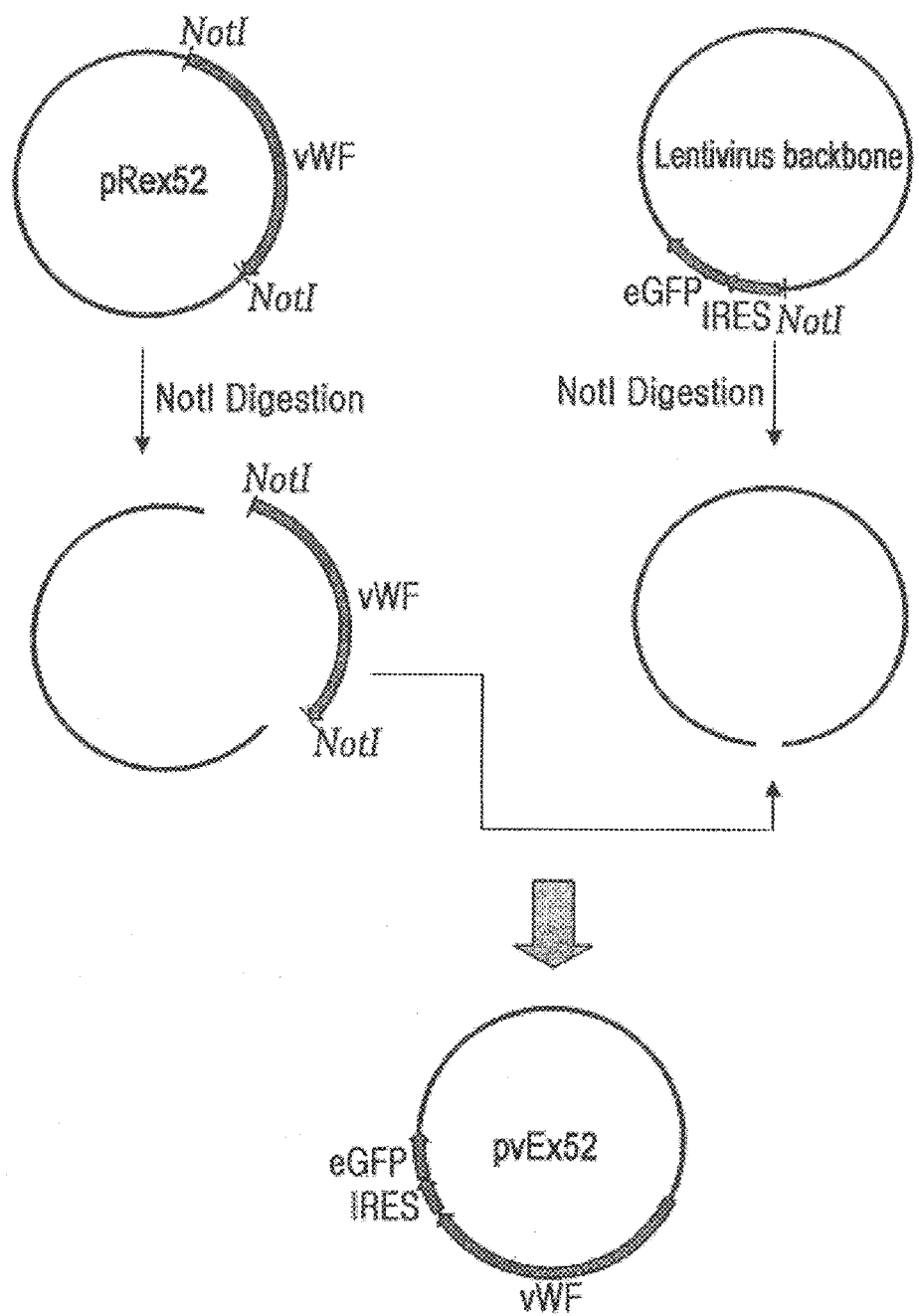
FIG. 10 illustrates a process of manufacturing a lentiviral vector comprising a vWF gene according to an embodiment of the present invention.
Figure 11:
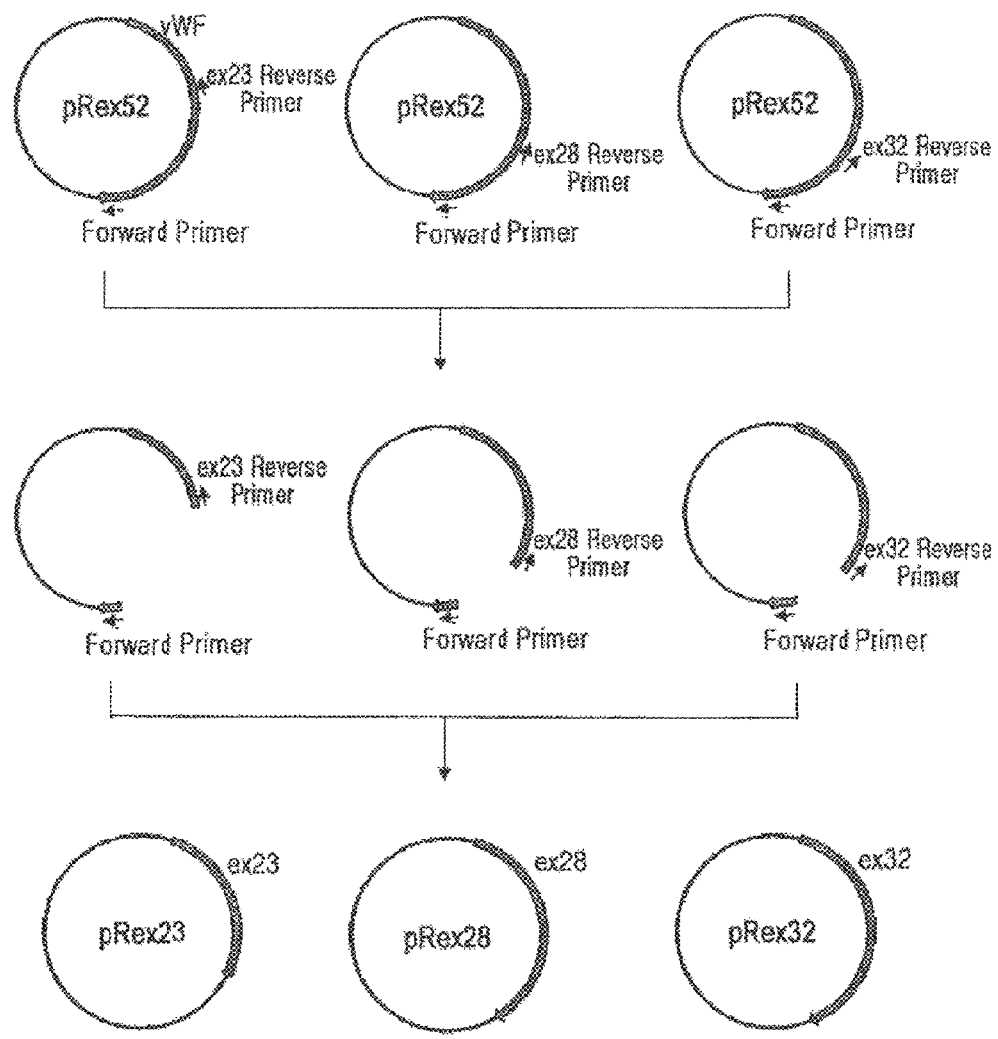
FIG. 11 illustrates a process of manufacturing vectors comprising pRex23, pRex28 and pRex32 comprising variants of vWF according to an embodiment of the present invention.

To manufacture Lentivirus vector comprising vWF (von Willebrand Factor) gene, the pRex52 and lentivirus backbone were digested by Not1, vWF fragments were ligated in Not1 site of lentivirus backbone, and pvEx52 was manufactured. This process of manufacturing was represented in FIG. 10. A particular map of pvEx52 as a result of FIG. 10 is shown in FIG. 1. vWF gene is located between long terminal repeats (LTRs) and fused into IRES-eGFP of a viral vector. vWF variants were manufactured from the pRex52 using PCR (polymerase chain reaction). The PCR was performed using dNTP 25 mM, phosphorylated primers 10 μg, 2 mM $Mg^{2+}$, DNA template, and pfuUltraTMII Fusion™ HS DNA Polymerase (Agilent Technologies, USA). The PCR had 50 μg of Total volume and was performed under following conditions: 5 min at 95° C.; 18 cycles of 30 sec at 95° C., 30 sec at 52° C. and 30 sec at 72° C. per 1 Kb; and 10 min at 72° C. For manufacturing the vWF variants, a forward primer sequence was 5'-CGT GATGAGACGCTCCAG-3' (SEQ ID NO.: 13), and reverse primer sequences were 5'-TTTTCTGGTGT-CAGCACACTG-3' (SEQ ID NO.: 14; pRex23), 5'-AGGTG-CAGGGGAGAGGGT-3' (SEQ ID NO.: 15; pRex28) and 5'-AGAGCACAGTTTGTGGAG-3' (SEQ ID NO.: 16; pRex32), respectively. After PCR, amplified products were isolated by using PCR removal kit (Qiagen, USA) and ligated with ligase (Takara, JAPAN) at 15° C. for approximately 24 hour to manufacture pRex23, pRex28 and pRex32. This process of manufacturing is shown in FIG. 11. The ligated mixture was transformed into TOP10.

Figure 12:
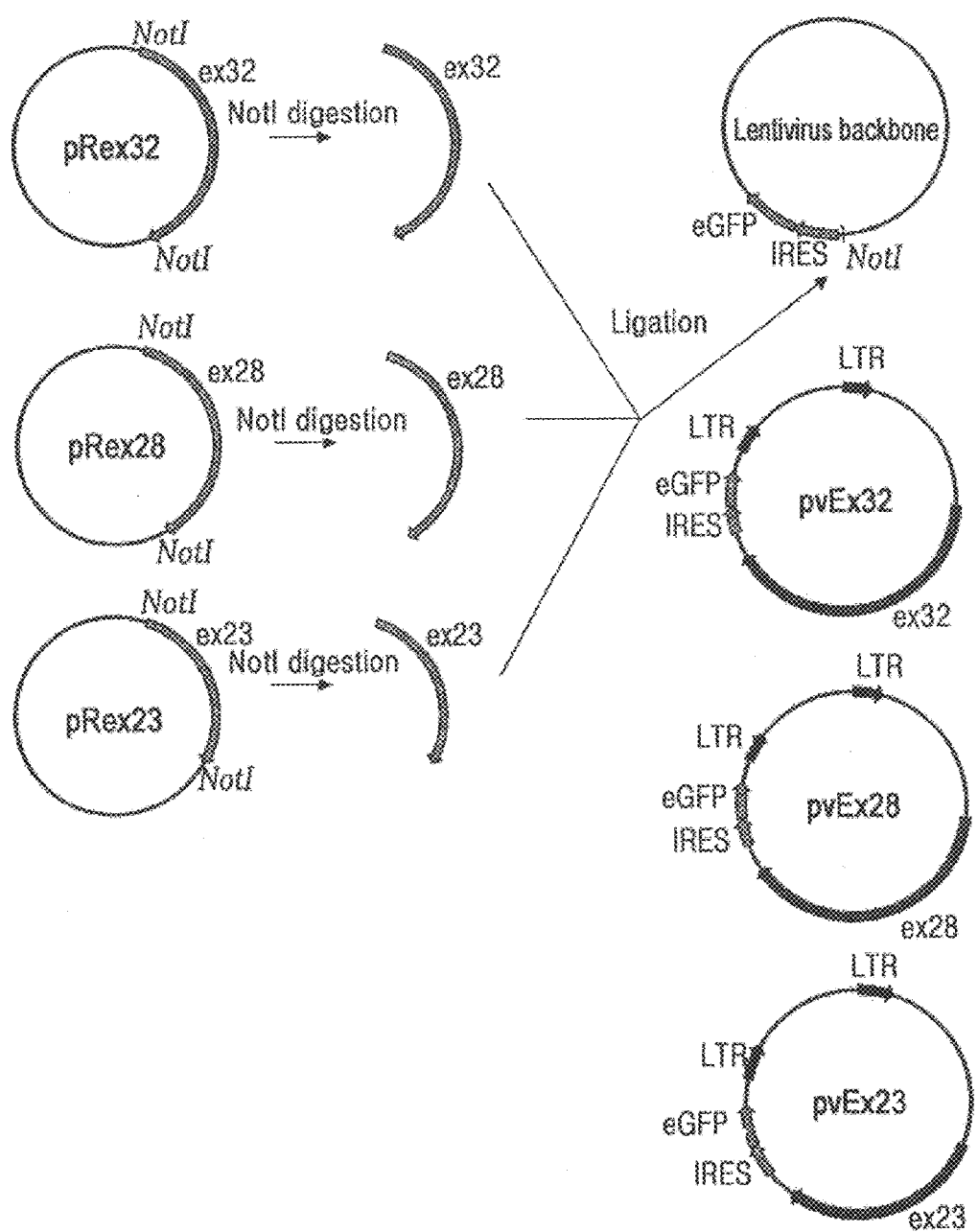
FIG. 12 illustrates a process of manufacturing lentiviral vectors pvEx23, pvEx28 and pvEx32 comprising variants of vWF according to an embodiment of the present invention.
Figure 13:
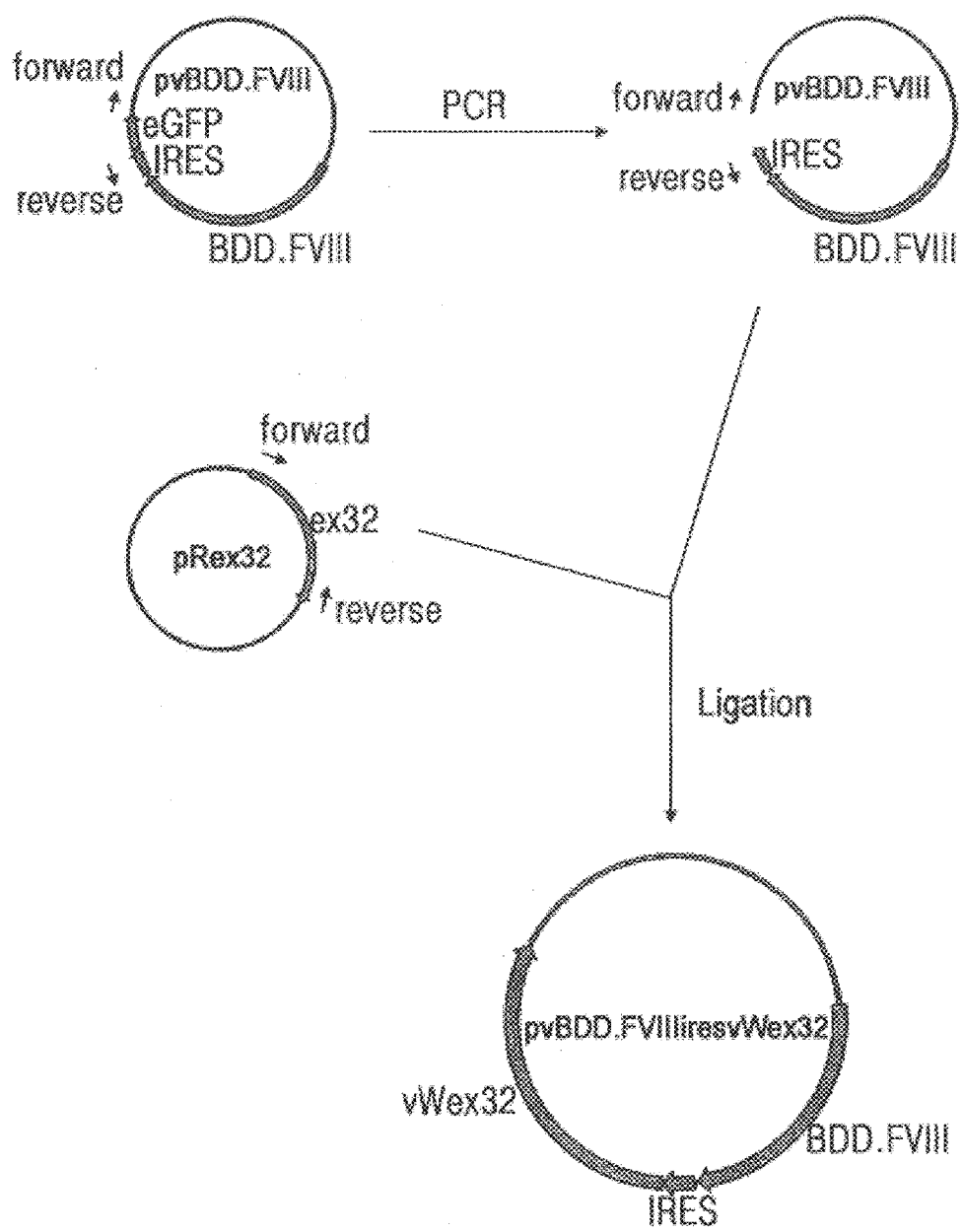
FIG. 13 illustrates a process of manufacturing a pvBDD.FVIII.vWEx32 lentiviral vector comprising BDD.FVIII and vWF variant genes.

To manufacture Lentivirus vector comprising vWF variants gene, the pRex23, pRex28 or pRex32 and lentivirus backbone were digested by Not1, the vWf fragments from the pRex23, pRex28 or pRex32 were ligated into Not1 site of lentivirus backbone, and pvEx23, pvEx28 and pvEx32 were manufactured. This process of manufacturing is shown in FIG. 12.

pvBDD.FVIII has a form that IRES-eGFP is located after the BDD.FVIII. Only the eGFP was deleted from the pvBD-D.FVIII by PCR and thereinto vWF variant was inserted to produce pvBDD.FVIII.vWEx32. This process of manufacturing is shown FIG. 13.

The TOP10 was used as a host in the transformation. To co-express BDD.FVIII and vWF21, IRES (internal ribosomal entry site) sequence was inserted after BDD.FVIII and thereafter vWF32 was inserted. Therefore, co-expression of two proteins under one promoter is possible, and the vWF32 expressed after BDD.FVIII plays a role in helping an activity and function of BDD.FVIII.

Example 2

Production of Virus

Vesicular stomatitis G protein (VSV-G) pseudotyped HIV-1 was produced by cotransfecting 293T cells with gag-pol, tat, rev, VSV-G and transfer vector using quinquepartite plasmid transient transfection method (Park and Choi, 2004 Mol. Cells 17, 297-303). 293T cells were subcultured at a density of $4.5 \times 10^6$ cells on 100 mm plates 24 hours prior to transfection. The supernatant was replaced with culture medium comprising 10% FCS and 25 mM HEPES 4 hours prior to transfection. For transfection, packaging plasmid with Gag and Pol 10 μg, VSV-G plasmid 2 μg, Tat plasmid 1 μg, Rev plasmid 1 μg and transfer vector 10 μg were used. These DNAs were added in 62 μl of 2.5 M $CaCl_2$, the volume was set to 500 μl with water, and vortexed. This mixture was added with 500 11R of 2×HBS (281 mM NaCl, 100 mM HEPES, 1.5 mM $Na_2HPO_4$ pH 7.12), left for 30 min at room temperature, and then spread on 293T cells. 16 hours after transfection, the supernatant was replaced with RPMI of 10 mM HEPES buffer. After 48 hours, viruses produced and flowed to supernatant were harvested by using 0.45 μm filter.

Example 3

Titration of Virus $3 \times 10^5$ cells of NIH3T3 cells were placed on 60 $cm^2$ dishes, and after 20 hours serial dilutions of viral stocks were added in the cells. Total volume was set to 2 ml and 2 μg/ml of polybrene (Sigma-Aldrich, USA) was added. After 6 hours, the virus was removed, the cells were washed with DMEM comprising 2% FCS to remove the virus completely, and the cells were put into an incubator. After 2 days, the cells were separated with 0.25% trypsin, washed with 1×PBS, and fixed with 3.7% formaldehyde. Percent of $eGFP^+$ radiating in the infected cells was determined using FACScan™ (Becton Dickinson, USA Immunocytometry System) and CellQuest program (Becton Dickinson, USA), and then the titer of virus was calculated using the following formula: (2× a number of cells×Percent of $eGFP^+$ cells)+quantity of virus.

Example 4

Concentration of Virus

Figure 3:
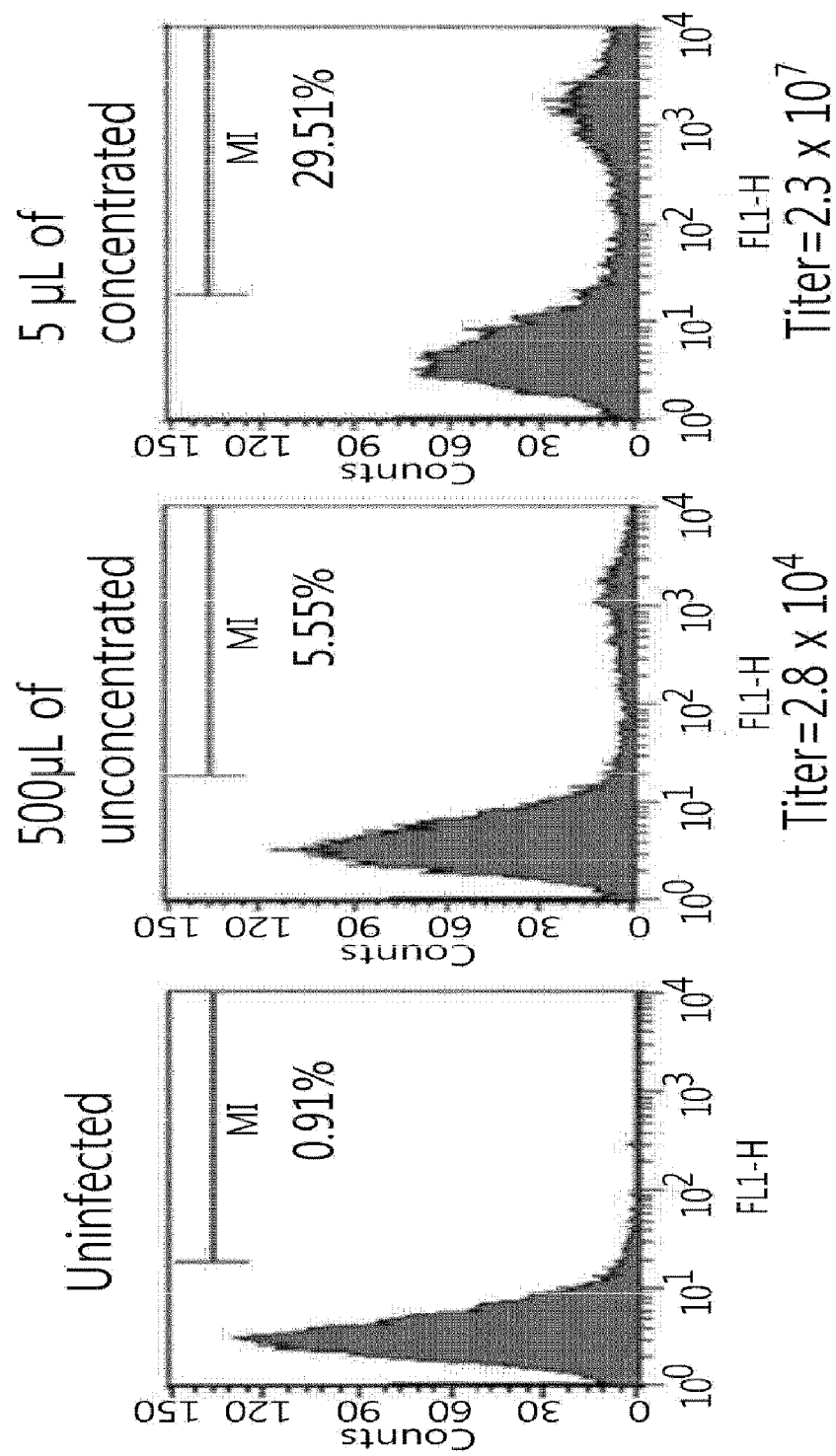
FIG. 3 concentration of vWF-expressing HIV-1 according to an embodiment of the present invention.

The filtered virus was transferred to polyallomer tubes and ultracentrifuged at 50,000×g in SW28 rotor for 1.5 hour at 4° C. The pellet was resuspended in a small volume of medium. Then, the tube was covered with Parafilm®, and left to stand at 4° C. for 24 hours. For extended storage, the viral stocks were stored at −80° C. FIG. 3 represents concentration of vWF-expressing HIV-1 according to an embodiment of the prevent invention. 500 μl of non-concentrated (middle) and 5 μl of concentrated (right) of vWF-expressing lentivirus supernatants were used to transduce Jurkat cells. The fraction of eGFP+ cells among the transduced cells was determined by flow cytometry.

Example 5

Transduction of Cells

Figure 5:
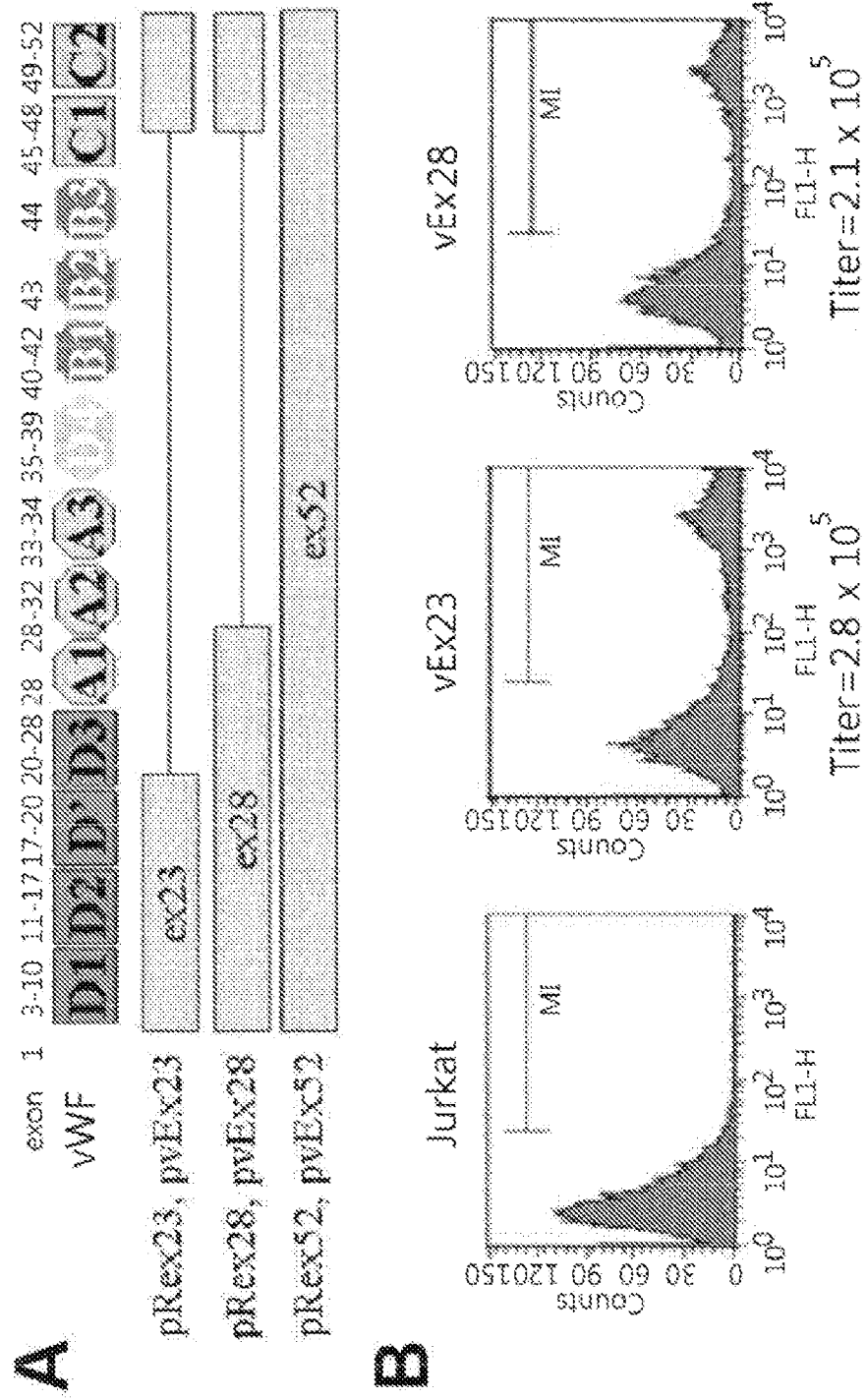
FIG. 5A-B schematically represent the deletion constructs of vWF according to an embodiment of the present invention. pRex23 and pRex28 were generated from pREP7-vWF (generously provided by Dr. Subrata Banerjee) by deleting exons 24-46 and 29-46, respectively, and pvEx23 and pvEx28 were generated in the same way from pvEx52 (FIG. 5A). The sequences were deleted by PCR using the forward primer 5'-CGTGATGAGACGCTCCAG-3' (SEQ ID NO.: 17), and the reverse primer of Ex23PR 5'-TTTTCTGGTGTCAGCA-CACTG-3' (SEQ ID NO.: 18) for pRex23 and pvEx23, and Ex28PR 5'-CAGGTGCAGGGGAGAGG-3' (SEQ ID NO.: 19) for pRex28 and pvEx28. pvEx23 and pvEx28 were then used to generate VSV-G pseudotyped HIV-1 with packaging vectors, and titrated in Jurkat cells. 35.02% and 26.30% of the cells proved to be positive for eGFP when 500 µl of the viral supernatants of vEx23 and vEx28, respectively, were employed for transduction (FIG. 5B).

The cells were counted by hemocytometer and plated in 24-well or 6-well plates at the desired cell number. Viral supernatants were added to the cells at the desired multiplicity of infection (MOI). At this time, the total volume was adjusted to the desired volume with the culture medium, and polybrene was added at a concentration of 2 µg/ml. The infection was performed in the presence of 5% $CO^2$ for 6 hours at 37° C. After infection, the cells were washed with the medium. FIG. 5 is a schematic showing deleted constructs of vWF according to an embodiment of the prevent invention. (A) pRex23 and pvEx23 were constructed by deleting exons 24-46, and pRex28 and pvEx28 were generated by deleting exams 29-46, from pRex52 and the lentiviral vector, respectively. (B) vEx23 and vEx28 were generated from pvEx23 and pvEx28, respectively, and 500 µl of viral supernatants were used to transduce Jurkat cells. The percentages of cells transduced were analyzed by FACS (Fluorescence-activated cell sorting).

Example 6

Isolation of DNA and RNA

Figure 2:
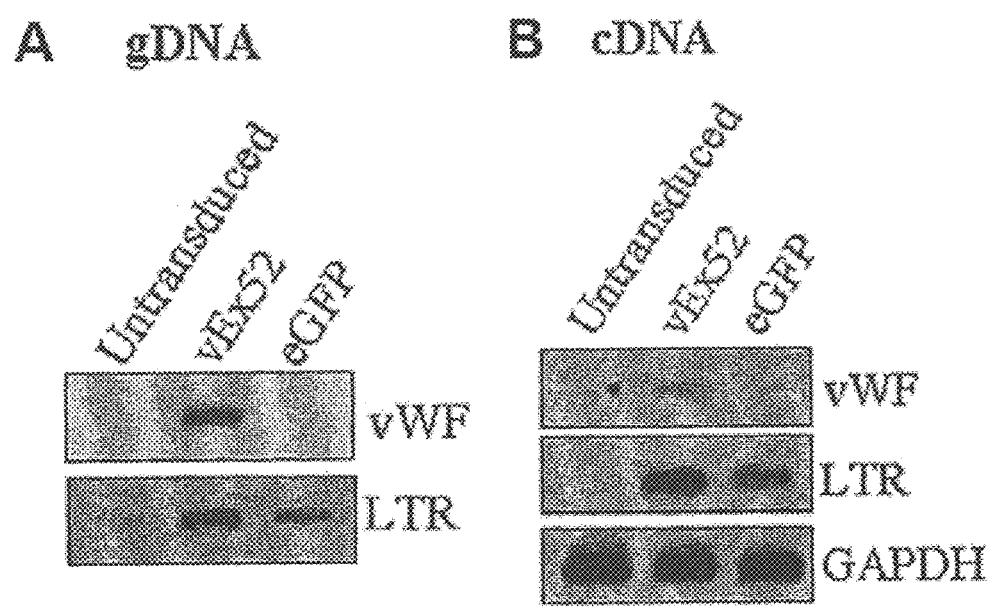
FIG. 2A-2B illustrate integration (gDNA, FIG. 2A) and transcription (cDNA, FIG. 2B) of vWF from transduced COS-1 cells gene according to an embodiment of the present invention.

Genomic DNA was prepared with 500 µl of lysis buffer (0.1 M Tris HCl, pH 8.5, 5 mM EDTA, 0.2% SDS, 200 mM NaCl and 100 µg/ml protease K). It was precipitated with isopropanol and washed with 75% ethanol. RNA was prepared with Trizol® reagent (Invitrogen™, USA) and cDNA was synthesized using ImPromII™ (Promega, USA). PCR was carried out with Pfu (SolGent, Republic of Korea) in a total volume of 50 µl containing 1× reaction buffer, 25 mM each dNTP, 10 µM each primers, 2 mM $Mg^{2+}$, and DNA template. FIG. 2 represents integration and transcription of vWF from transduced COS-1 cells according to an embodiment of the prevent invention. The COS-1 cells were transduced with lentivirus expressing vWF. (A) Integration of the transduced vWF gene was detected in the genomic DNA of transduced COS-1 cells by PCR for 421-bp of vWF and 227-bp of LTR. (B) cDNA was prepared from the transduced cells and amplified with primers specific for 421-, 227- and 187-bp of vWF, LTR, and GAPDH, respectively. vEx52: transduced with vEx52, eGFP: transduced with eGFP-expressing lentivirus.

Example 7

Plasmid Transfection

DNAs (pRex23, pRex28 and pRex32) for transfection were added into 50 µl of 150 mM NaCl on 12-well plate, vortexed and spun down. This mixture was added with PEI in 3 times volume of DNA, vortexed and spin down again. This mixture was left for 10 min at room temperature, and was dropped on the cells carefully.

Example 8

Immunocytochemistry

Transduced cells were grown on glycogen-coated coverslips in 6-well tissue culture plates. The cells were fixed in cooled 100% methanol, washed with TBS [50 mM Tris-HCl (pH 7.4), 150 mM NaCl], quenched in fresh 0.1% sodium borohydride in TBS for 5 min and washed three times with TBS for 5 min. The cells were blocked with blocking buffer (10% horse serum, 1% bovine serum albumin, 0.02% $NaN_3$ in 1×PBS) for 60 min and washed for 5 min with TBS. Primary vWF antibody (Abcam®, USA) was diluted in 1% BSA in TBS and incubated overnight with the cells at 4° C. After washing the cells three times for 5 min with TBS, they were labeled with secondary goat-antimouse IgG TRITC antibody (Santa Cruz Biotechnology, USA) in 1% BSA in TBS for 30 min at room temperature covered with aluminum foil. They were then washed 3 times with TBS for 5 min and mounted on slides using a ProLong® Antifade Kit (Cell Signaling, USA).

Figure 4:
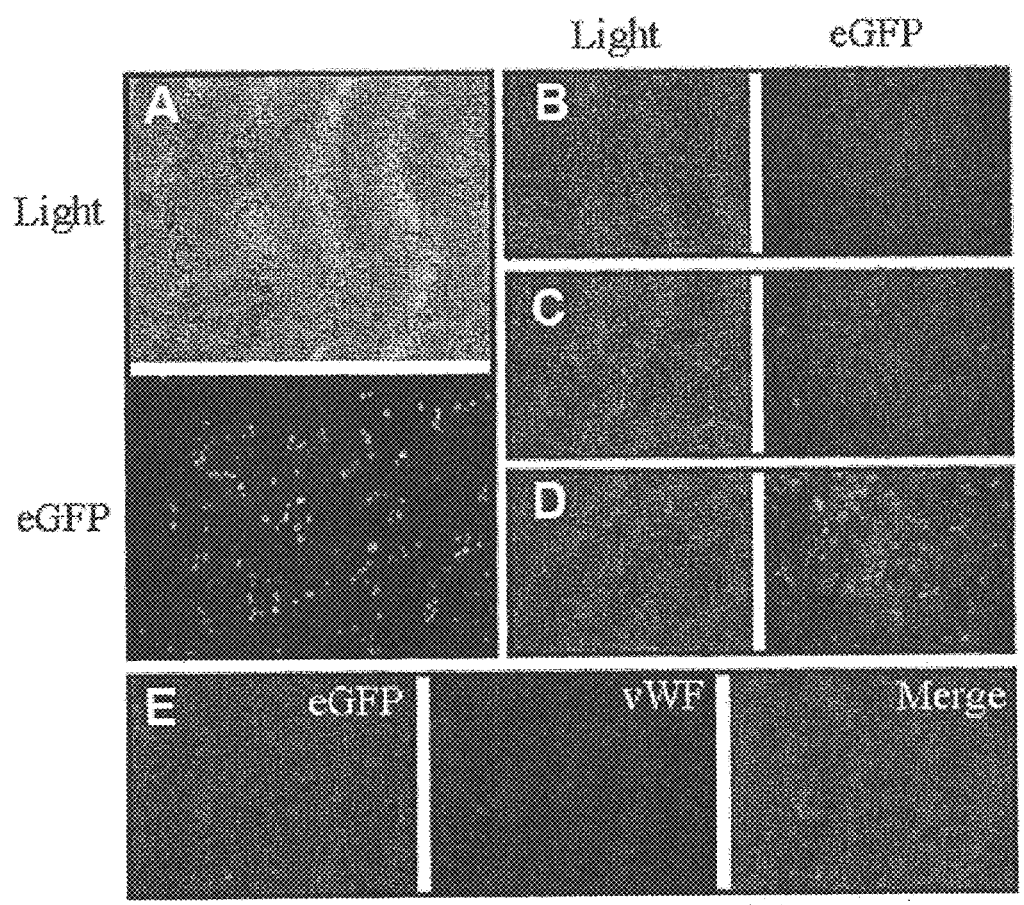
FIG. 4A-4E illustrate transduction of pseudotyped HIV-1 expressing vWF according to an embodiment of the present invention. Transfection of the vectors resulted in lentivirus production, as indirectly confirmed by expression of eGFP (FIG. 4A). The transduction and expression of both the non-concentrated and the concentrated vEx52 were also visualized with fluorescence light from the eGFP expression (FIG. 4B-D). In order to verify vWF expression from vEx52, COS-1 cells were transduced with vEx52 at a MOI of 0.5 and labeled with human vWF antibody, followed by TRITC staining (FIG. 4E).

FIG. 4 represents transduction by pseudotyped HIV-1 expressing vWF according to an embodiment of the prevent invention. (A) 293T cells were cotransfected with plasmids harboring viral components for virus production including a transfer vector that harbored vWF-IRES-eGFP. eGFP from the transfer vector was visualized under a fluorescence microscope at 10× magnifications. (B) Jurkat cells were visualized under a microscope with bright and fluorescence light. (C) Jurkat cells were transduced with 500 μl of non-concentrated vWF-expressing pseudotyped HIV-1 and visualized under a microscope. (D) Jurkat cells were transduced with 5 μl of 160-fold concentrated vWF-expressing pseudotyped HIV-1 and visualized under the white and fluorescence light. (E) COS-1 cells were transduced with vWF-pseudotyped HIV-1 at a MOI of 0.5. eGFP was visualized under a fluorescence microscope (left). vWF was visualized by staining vWF with antibody and TRITC (middle). The detected vWF was not from the COS-1 cells but from the transferred gene (right).

BDD.FVIII deleting B domain from sequence of FVIII was prepared and inserted into lentivirus vector. For expression of lentivirus, the BDD.FVIII was expressed together with gag, pol, VSV-G, tat, and rev in 293T cells to produce lentivirus expressing BDD.FVIII. The transfected cells may express BDD.FVIII. Conclusively, the expression was confirmed by measuring activity of FVIII. Production and infection of virus were confirmed indirectly by expression of eGFP in the vector. FIG. 7 is a photograph representing result of eGFP expression in order to confirm expression of FVIII according to an embodiment of the prevent invention (correspond to FIG. 4 (*a*)). Production and infection of virus were confirmed indirectly by expression of eGFP.

Example 9

Measurement of Factor VIII Activity

Activated FVIII activity (FVIII:C) was measured by Coatest® VIII:C/4 kit (DiaPharm, Italy). One volume of phospholipids and 100 mg/l ciprofloxacin was mixed with 5 volumes of Factor IXa and Factor X. The mixture 50 μl was placed in 96-well microtiter plates, added with 25 μl of cell culture supernatant, incubated for 5 min at 37° C. And then, the mixture was added with 25 μl of 0.025 mol/L CaCl2, incubated for 5 min at 37° C., added with 50 μl of S-2765 and 1-2581, and incubated for 10 min at 37° C. The incubation was stopped by 20% acetic acid, and the activity of FVIII was measured at 405 nm. A standard curve was made with each experiment using known amounts of recombinant human FVIII.

FIG. 6 represents detection of the activity of secreted functional FVIII. (A) 293T cells were co-transfected with pREP7-BDD.FVIII and pRex23, pRex28, or pRex52. The supernatants of the transfected cells were collected and quantitated for FVIII activity. (B) K562 cells were co-transduced with HIV-1-BDD.FVIII and vEx23, vEx28 or vEx52 at a MOI of 1.5. The supernatants of the transduced cells were collected and screened for FVIII activity. The data are expressed as the means±S.E. of at least three independent experiments. (C) RT-PCR was performed with RNAs from the transduced cells. B-domain-deleted FVIII yields a product of 1.1 Kb. vEx23: transduced with vEx23, vEx28: transduced with vEx28, vEx52: transduced with vEx52.

Example 10

Figure 8A:
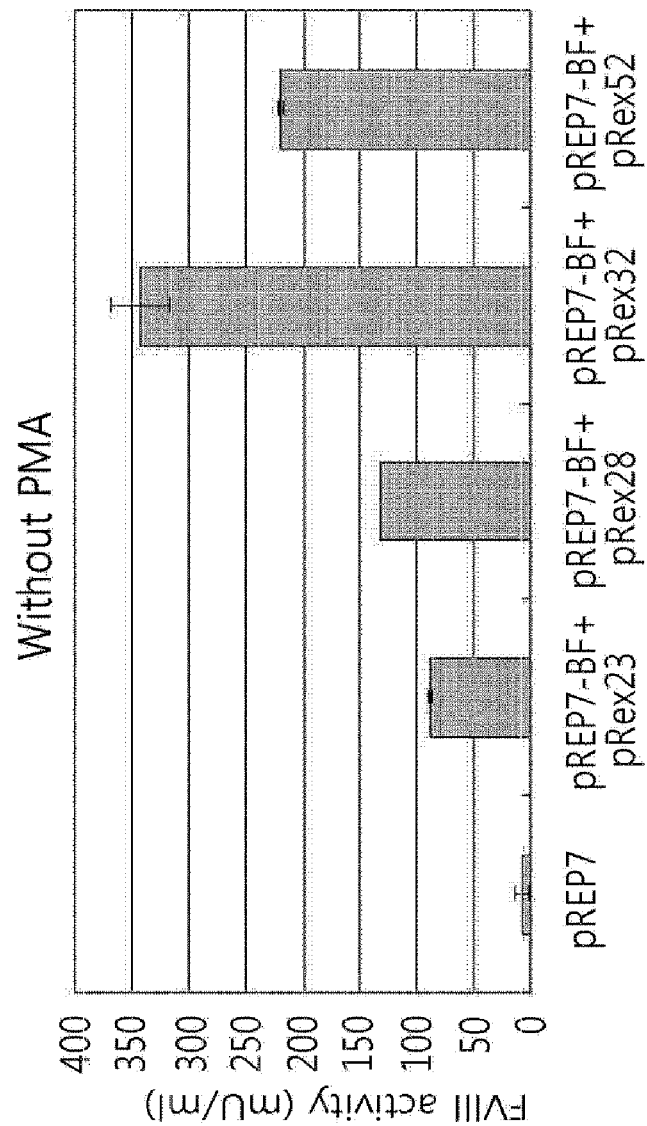
FIG. 8 illustrates activation of FVIII by different mutant vWFs determined by chromogenic assay according to an embodiment of the present invention (FIG. 8A represents activities of FVIII in normal state (without damage) and FIG. 8B represents activities of FVIII treated with PMA (phorbol ester) in damaged state)
Figure 8B:
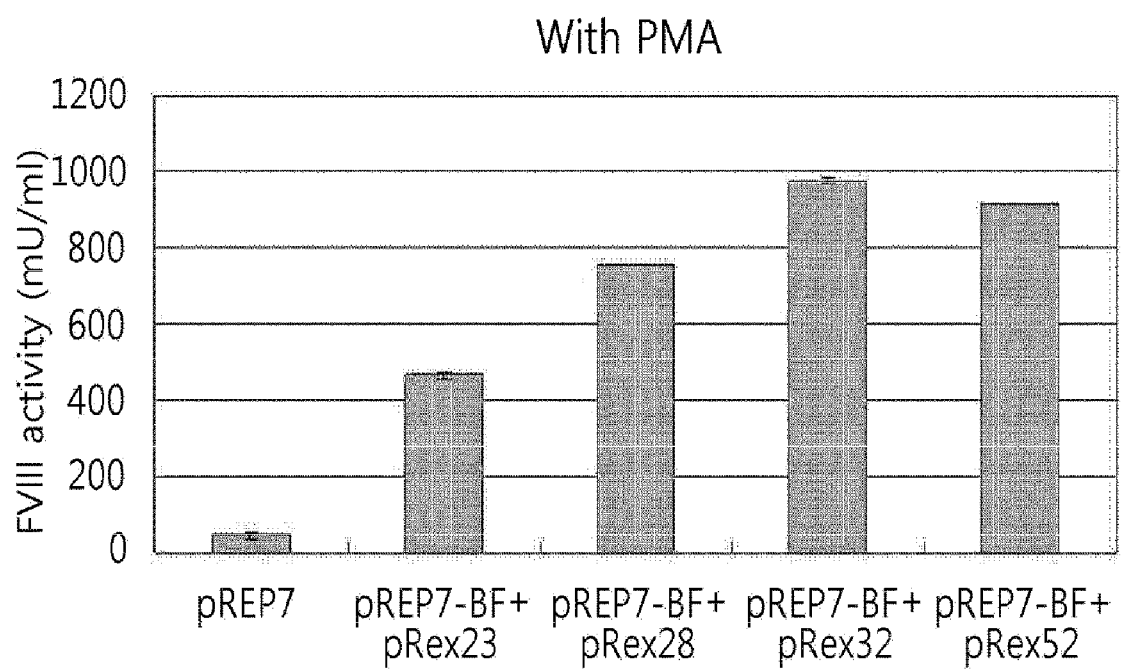

Measurement of Factor VIII Activity after PMA Treatment pRex23, pRex28 and pRex32 are named for Von Willebrand Factors deleting C-terminal domains from exon 23, exon 28 and exon 32, respectively. pRex52 is named for full length of vWF. They were co-expressed with pREP7-BF carrying a von Willebrand factor vector and the activity of secreted FVIII was determined. As a result, pREP7-BF and pRex32 had the greatest activity of secreted FVIII (FIG. 8). FIG. 8 represents the results of measuring the activity of FVIII for each vWF variant by Chromatography Assay. HeLa cells were transfected with pREP7; pREP7-BF and pRex23; pREP7-BF and pRex28; pREP7-BF and pRex32; and pREP7-BF and pRex52, and then functional activities of FVIII secreted out in supernatant were measured. FIG. 8A represents the results of measuring the activities of FVIII in normal state (without damage). The activities of all FVIIIs were increased as compared with a basal level, and the 32 (pREP7-BF and pRex32) was the greatest. FIG. 8B represents the activities of FVIII treated with PMA (phorbol ester) in damaged state. The secretion of all FVIIIs was induced at least 3 times and marked a remarkable difference as compared with basal level. The result means that FVIII secretion is induced greatly in damaged state, but not in normal state, which give a very useful advantage in real clinics of hemophilia.

Result 1: Lentivirus Production 8.8 Kb of von Willebrand Factor cDNA was cloned into the HIV-1-based lentivirus between the two long terminal repeats to create pvEx52 (LTRs) (FIG. 1). The vWF cDNA was excised from vW-8 (ATCC® #59126) using EcoR1 and Sac1 and cloned into the lentiviral vector. The vWF gene was fused with IRES-eGFP, thus permitting the use of enhanced green fluorescence protein (eGFP) as an indirect indicator of virus production after transfection into 293T cells together with the other viral genes required for packaging viral particles (Parolin et al., 1996; Yee et al., 1994). The packaging vector harbored gag and pol under the control of the CMV promoter, and the tat and rev of HIV-1 were expressed separately under the control of the CMV promoter. We used the vesicular stomatitis virus G protein (VSV-G) instead of HIV-1 env (Hofmann et al., 1999).

Result 2: Transduction of VSV-G Pseudotyped HIV-1

COS-1 cells were transduced with vEx52, the lentivirus carrying the complete vWF, or HIV-1-eGFP, the eGFP-expressing lentivirus. Genomic DNA was isolated from the transduced COS-1 cells, and PCR was conducted using primers specific for the human vWF gene and HIV-1 LTR. vWF could be amplified only from the vEx52-transduced cells, whereas LTR could be amplified from both vEx52 and HIV-1-eGFP-transduced cells (FIG. 2A). In addition, RNA was prepared from the transduced cells, with which cDNA was synthesized and PCR for vWF and LTR was conducted (FIG. 2B). The result of RT-PCR accorded with the amplifications from the PCR of the genomic DNA. vWF was amplified only from the vEx52-transduced cells, and LTR was detected from both vEx52 and HIV-1-eGFP-transduced cells.

Result 3: Expression of vWF from Transduced Lymphoblast Cells and Concentration of vEx52

Jurkat cells were plated at $2 \times 10^5$ and transduced with 500 µl of non-concentrated vEx52 virus. FACS analysis showed that 5.55% of the cells were positive for GFP expression (FIG. 3). After the virus suspension was concentrated by a factor of 160 by ultracentrifugation at 50,000×g, 5 µl of concentrated virus was employed to transduce an equal number of Jurkat cells, resulting in a yield of 29.51% eGFP+ (FIG. 3). By concentrating the vEx52 virus, the titer increased from $2.8 \times 10^4$ particles/ml to $2.3 \times 10^7$ particles/ml. Transfection of the vectors resulted in lentivirus production, as indirectly confirmed by expression of eGFP (FIG. 4A). The transduction and expression of both the non-concentrated and the concentrated vEx52 were also visualized with fluorescence light from the eGFP expression (FIG. 4B-D). In order to verify vWF expression from vEx52, COS-1 cells were transduced with vEx52 at a MOI of 0.5 and labeled with human vWF antibody, followed by TRITC staining (FIG. 4E). In addition, in order to determine whether the transduced constructs were maintained for an extended period of time, $1 \times 10^5$ Jurkat cells were transduced at a MOI of 0.5. After 4 days, 38.27% of the cells were shown by FACS analysis to be positive for eGFP. When analyzed on days 9, 15, 35, 50 and 90 post-transduction, 33.01%, 11.99%, 11.32%, 6.13%, and 5.56%, respectively of the cells were eGFP+(data not shown).

Result 4: Construction of Domain-Deleted vWF pRex23 and pRex28 were generated from pREP7-vWF (generously provided by Dr. Subrata Banerjee) by deleting exons 24-46 and 29-46, respectively, and pvEx23 and pvEx28 were generated in the same way from pvEx52 (FIG. 5A). The sequences were deleted by PCR using the forward primer 5'-CGTGATGAGACGCTCCAG-3' (SEQ ID NO.: 17), and the reverse primer of Ex23PR 5'-TTTTCTGGTGTCAGCACACTG-3' (SEQ ID NO.: 18) for pRex23 and pvEx23, and Ex28PR 5'-CAGGTGCAGGGGAGAGG-3' (SEQ ID NO.: 19) for pRex28 and pvEx28. pvEx23 and pvEx28 were then used to generate VSV-G pseudotyped HIV-1 with packaging vectors, and titrated in Jurkat cells. 35.02% and 26.30% of the cells proved to be positive for eGFP when 500 µl of the viral supernatants of vEx23 and vEx28, respectively, were employed for transduction (FIG. 5B).

Result 5: Functional Activity of the Secreted FVIII

Figure 6:
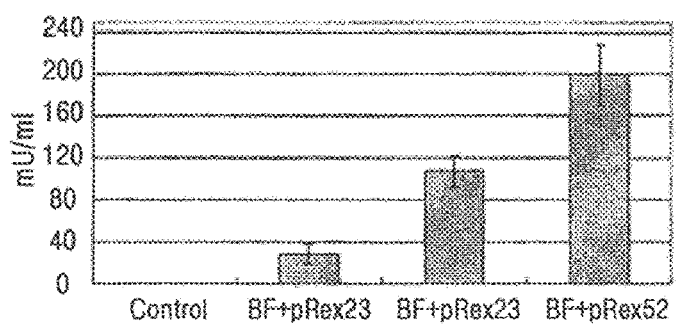
FIG. 6A-C illustrate detection of the activity of secreted functional coagulation Factor VIII (FVIII) according to an embodiment of the present invention. Levels of FVIII activity of 28.89±18.86, 107.22±30.64, and 199.44±58.93 were obtained from transfection with pRex23, pRex28, and pRex52, respectively (FIG. 6A). FVIII activity in the supernatants of the transduced cells was 28.33±5.50 for the vEx52-transduced cells, and 33.89±3.93 and 53.33±9.43, respectively for the vEx23- and vEx28-transduced cells (FIG. 6B). K562 cells were co-transduced with vBDD.FVIII, the BDD-FVIII expressing HIV-1, along with vEx23, vEx28, or vEx52 at a MOI of 1.5. RT-PCR with RNA from the transduced cells confirmed expression of the transduced FVIII (FIG. 6C)
Figure 6:
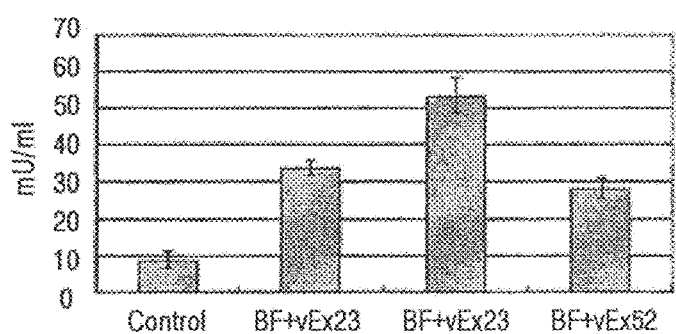
Figure 6:
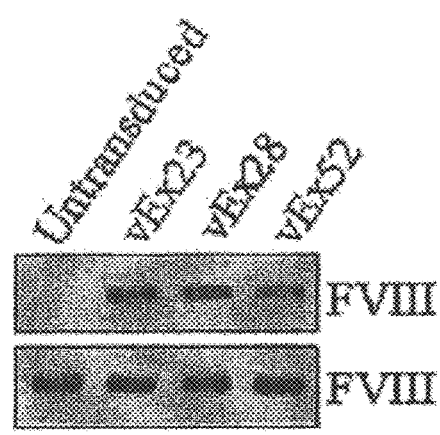
Figure 7:
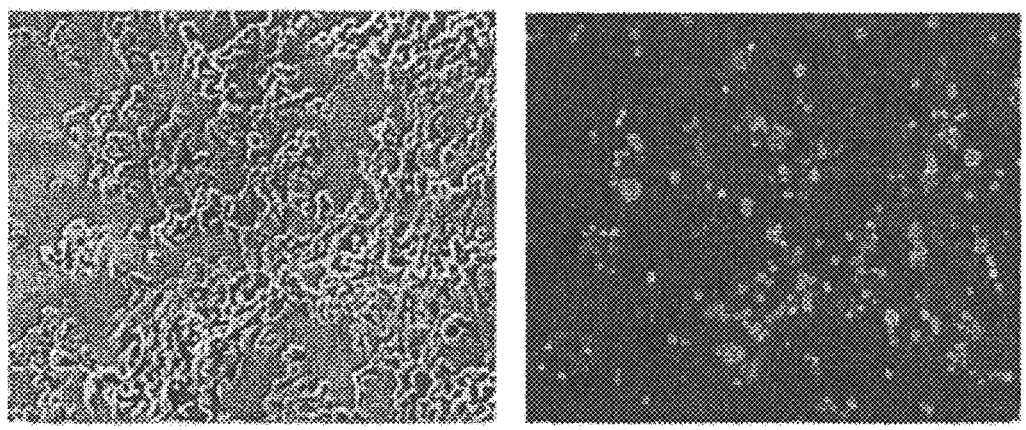
FIG. 7 illustrates expression of eGFP tested to confirm the expression of FVIII according to an embodiment of the present invention.

In order to examine the effects of domain-deleted vWF on the secretion of FVIII, 293T cells were transfected with pREP7-BDD.FVIII along with one pRex23, pRex28, or pRex52. After 48 h of transfection, the supernatants were collected and screened for functional FVIII activity in chromogenic assays. Levels of FVIII activity of 28.89±18.86, 107.22±30.64, and 199.44±58.93 were obtained from transfection with pRex23, pRex28, and pRex52, respectively (FIG. 6). Therefore, the functional activity of the secreted FVIII declined as more of vWF was deleted. Next, we assessed the effects of domain-deleted vWF when it was transduced as a component of vWF lentivirus. K562 cells were co-transduced with vBDD.FVIII, the BDD-FVIII expressing HIV-1, along with vEx23, vEx28, or vEx52 at a MO1 of 1.5. RT-PCR with RNA from the transduced cells confirmed expression of the transduced FVIII (FIG. 6). FVIII activity in the supernatants of the transduced cells was 28.33±5.50 for the vEx52-transduced cells, and 33.89±3.93 and 53.33±9.43, respectively for the vEx23- and vEx28-transduced cells (FIG. 6). These data suggest that the deleted form of vWF, vEx28, is the most efficient at promoting secretion of FVIII via interaction of its minimal essential domains with FVIII.

As described, in accordance with the present invention, coagulation Factor VIII (FVIII) can be effectively expressed in a viral vector and the FVIII activity can be significantly enhanced using mutant von Willebrand Factor (vWF) with a reduced size. Further, the viral vector of the present invention may be effectively used to treat hemophilia through gene therapy. The coexpression of FVIII and vWF may be very useful in clinical applications such as gene therapy for hemophilia A treatment.

While the present invention has been particularly shown and described with reference to exemplary embodiments thereof, it will be understood by those skilled in the art that various changes in form and details may be made therein without departing from the spirit and scope of the present invention as defined by appended claims.

What is claimed is:

1. A mutant von Willebrand factor (vWF32) having the amino acid sequence of SEQ ID NO: 6 in which exons 33-48 of vWF are deleted.

2. A mutant vWF32 gene having a base sequence encoding for a protein having the amino acid sequence of SEQ ID NO: 6.

3. The mutant vWF32 gene as set forth in claim 2, wherein the mutant vWF32 gene has the base sequence of SEQ ID NO: 5.

* * * * *